United States Patent
Radjy

(10) Patent No.: US 9,429,559 B2
(45) Date of Patent: Aug. 30, 2016

(54) SYSTEMS, METHODS AND APPARATUS FOR OBTAINING DATA RELATING TO CONDITION AND PERFORMANCE OF CONCRETE MIXTURES

(71) Applicant: QuipIP, LLC, Pittsburgh, PA (US)

(72) Inventor: Farrokh F. Radjy, Pittsburgh, PA (US)

(73) Assignee: QUIPIP, LLC, Pittsburgh, PA (US)

( * ) Notice: Subject to any disclaimer, the term of this patent is extended or adjusted under 35 U.S.C. 154(b) by 0 days.

(21) Appl. No.: 14/810,748

(22) Filed: Jul. 28, 2015

(65) Prior Publication Data
US 2016/0018383 A1 Jan. 21, 2016

Related U.S. Application Data

(63) Continuation-in-part of application No. 14/458,897, filed on Aug. 13, 2014.

(60) Provisional application No. 61/932,979, filed on Jan. 29, 2014.

(51) Int. Cl.
*G01N 33/38* (2006.01)

(52) U.S. Cl.
CPC ........ *G01N 33/383* (2013.01); *Y10T 29/49826* (2015.01)

(58) Field of Classification Search
CPC ............... G01N 11/00; G01N 33/383; G01N 2001/0046; B28B 23/0031
See application file for complete search history.

(56) References Cited

U.S. PATENT DOCUMENTS

| | | | |
|---|---|---|---|
| 6,324,904 B1 * | 12/2001 | Ishikawa | E21B 47/011 257/E29.022 |
| 6,642,906 B1 * | 11/2003 | Machalek | H01Q 9/28 343/872 |
| 6,958,693 B2 * | 10/2005 | Rothgeb | A47L 15/4297 134/113 |
| 7,551,058 B1 * | 6/2009 | Johnson | G01N 27/226 340/10.41 |
| 7,777,628 B2 * | 8/2010 | Tilson, Jr. | B28B 23/00 235/375 |
| 7,804,406 B2 * | 9/2010 | Kaga | G01N 33/383 324/632 |
| 7,841,249 B2 * | 11/2010 | Tormoen | F16L 55/38 73/865.9 |
| 8,230,738 B2 * | 7/2012 | Radziszewski | B02C 17/1805 73/489 |
| 8,397,810 B2 * | 3/2013 | Verret | E21B 47/1015 166/250.12 |

(Continued)

OTHER PUBLICATIONS

Schaefer et al. Polymeric Materials for Adaptronic Fibre Modules, Session 4: Polymer Electronic Devices II, 2001, p. 98-103.*

(Continued)

*Primary Examiner* — Peter Macchiarolo
*Assistant Examiner* — Nathaniel Kolb
(74) *Attorney, Agent, or Firm* — Lucas & Mercanti, LLP; Jonathan A. Tyler

(57) ABSTRACT

A sensing device includes a shell comprising an elastomeric material, the shell including a first portion having a first end and a second portion having a second end. The shell may be egg-shaped. The first portion includes a conducting disc and a plate that includes a temperature sensor, a location sensor, and a micro-fiber composite sensor. The first portion also includes an antenna and a first electrode extending through a first hole in the first portion of the shell. The second portion includes a quantity of a metallic substance embedded on the inside surface of an end of the second portion, and a second electrode extending through a second hole in the second portion of the shell. The sensing device may be inserted into a concrete mixture, obtain measurements relating to the concrete mixture, and transmit data to a database.

16 Claims, 21 Drawing Sheets

(56) References Cited

U.S. PATENT DOCUMENTS

| | | | | |
|---|---|---|---|---|
| 8,661,909 B2* | 3/2014 | Chu | F16L 55/28 | 73/700 |
| 8,881,809 B2* | 11/2014 | Verret | E21B 47/10 | 166/250.12 |
| 8,939,020 B2* | 1/2015 | Townsend | G01M 17/02 | 73/146 |
| 2003/0227394 A1* | 12/2003 | Rothgeb | A47L 15/4297 | 340/870.01 |
| 2005/0056415 A1* | 3/2005 | Zillinger | E21B 47/06 | 166/66 |
| 2007/0096880 A1* | 5/2007 | Nagai | G06K 19/0717 | 340/10.41 |
| 2008/0041173 A1* | 2/2008 | Tormoen | F16L 55/38 | 73/866.5 |
| 2008/0067228 A1* | 3/2008 | Kaga | G01N 33/383 | 235/375 |
| 2008/0127742 A1* | 6/2008 | Mueller | G01L 19/0015 | 73/756 |
| 2009/0072978 A1* | 3/2009 | Tilson, Jr. | B28B 23/00 | 340/572.9 |
| 2009/0211754 A1* | 8/2009 | Verret | E21B 47/10 | 166/250.12 |
| 2010/0024518 A1* | 2/2010 | Radziszewski | B02C 17/1805 | 73/7 |
| 2010/0042389 A1* | 2/2010 | Farruggia | B08B 3/12 | 703/6 |
| 2012/0152025 A1* | 6/2012 | Chu | F16L 55/28 | 73/714 |
| 2012/0204625 A1* | 8/2012 | Beaupre | B28C 7/024 | 73/54.31 |
| 2014/0150542 A1* | 6/2014 | Townsend | G01M 17/02 | 73/146 |

OTHER PUBLICATIONS

Rupnow et al. Improving Portland Cement Concrete Mix Consistency and Production Rate through Two-Stage Mixing, National Concrete Pavement Technology Center Final Report, Sep. 2007.*

* cited by examiner

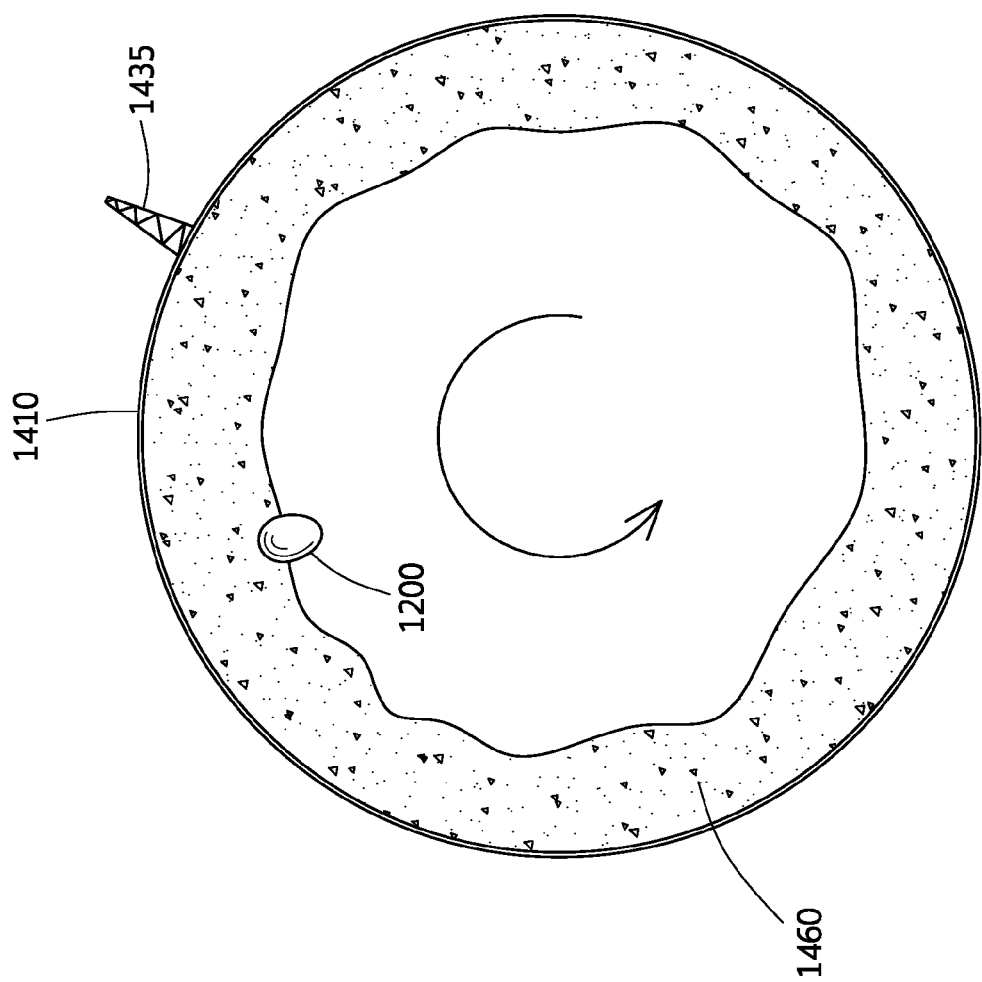

us 9,429,559 B2

SYSTEMS, METHODS AND APPARATUS FOR OBTAINING DATA RELATING TO CONDITION AND PERFORMANCE OF CONCRETE MIXTURES

CROSS REFERENCE TO RELATED APPLICATION

This application is a Continuation-in-Part of U.S. patent application Ser. No. 14/458,897, filed on Aug. 13, 2014, which claims the benefit of U.S. Provisional Patent Application No. 61/932,979, filed on Jan. 29, 2014, each of which is incorporated by reference herein in its entirety for all purposes.

TECHNICAL FIELD

This specification relates to a systems, methods, and apparatus for obtaining data relating to condition and performance of concrete.

BACKGROUND

Concrete is a composite material including coarse granular materials such as sands and stones embedded in a hard matrix of materials such as hydrated cements. Concrete production is performed by mixing these ingredients with water to make a fluid concrete. Typically, the fluid concrete is transported and put in place before it is hardened.

After the ingredients are mixed with water, the fluid concrete is continuously mixed during transportation by a mixer truck in order to maintain a quality of the concrete. However, there is no way to monitor the quality of the transported fluid concrete in real time. In addition, there is no way, in real time, of knowing the location where, in a given project, the fluid concrete is poured and what its mixture proportions and physical properties are at that location. Nor is it possible to track the progress of a poured volume, automatically and in real time in order to achieve better economics and improved construction efficiency.

After the fluid concrete is poured at an intended location, the concrete and the concrete construction industries generally use compression strength and other destructive tests to determine the quality of concrete placed at various projects in accordance to different engineering and mix design specifications. In most instances, the strength of the concrete is specified to reach certain strength at a curing age of 28 days. This is because the needed hardening or curing time for concrete is traditionally considered to be 28 days. Accordingly, in this day of instantaneous information and communications, the concrete industry still waits 28 days before knowing concrete quality.

SUMMARY

Embodiments of the present invention comprise a wireless device, and systems and methods for measuring a property of a concrete, both a fluid concrete inside a drum of a mixer truck, and hardened or hardening concrete in a structure, and transmitting data relating to the measurement. Embodiments of the present invention are specifically adapted for managing or controlling in real time the quality of a fluid concrete after it is made, during transportation, placement in a structure, and curing and hardening in the structure.

In European practice and sometimes in the United States, wet mixing is practiced, which means that complete mixing occurs at the plant and the truck mixer's function is agitation. In contrast, in the United States, concrete is dry-batched into the truck and the truck mixer does the mixing.

In accordance with an embodiment, the wireless device can be defined as comprising:
a shell;
at least one sensor inside the shell for measuring a property of a fluid concrete;
a transmitter connected to the sensor for transmitting data from the sensor; and
a power source inside the shell and connected to the sensor and the transmitter,
the device having a weight less than a buoyancy of the device such that the device floats at the surface of the fluid concrete.

Suitably, the shell is spherical.
Suitably, the shell has a diameter between about 1 and 10 cm.
Suitably, the shell is made of a metal or plastic.
Suitably, the sensor includes at least one of a temperature sensor, an accelerometer, a pH sensor, an inductance sensor, an impedance or resistivity sensor, a sonic sensor, a pressure sensor, or an elevation sensor.
Suitably, the device further includes a Global Positioning System unit.
Suitably, the device further includes a passive or active radio frequency identification tag inside the shell.
Suitably, the device further includes a date and time recorder inside the shell.
Suitably, the device further includes a data storage component inside the shell.
Suitably, the shell includes a layer of a form plastic.
Suitably, an upper half of the device is lighter than a lower half of the device.
Suitably, the transmitter is placed in the upper half of the device and the sensor is placed in the lower half of the device.

In accordance with another embodiment, a system for measuring a property of a fluid concrete in a mixer truck can be defined as comprising:
the device; and
an antenna mounted in a side of a drum of a mixer truck for transmitting data from the device inside the drum to outside the drum.
Suitably, the system further includes a data receiving device receiving the date from the antenna.
Suitably, the data receiving device is connected to a database storing the data.
In accordance with another embodiment, a method for measuring a property of a fluid concrete in a mixer truck can be defined as comprising:
putting a wireless measuring device in a drum of a mixer truck;
pouring a fluid concrete into the drum of the mixer truck; and
collecting data for a property of the fluid concrete by the wireless measuring device.
Suitably, the method further includes:
transmitting the data from the wireless measuring device; and
receiving the data from the wireless measuring device.
In accordance with another embodiment, a method for determining a property of a fluid concrete mixture can be defined as comprising:
receiving data from a device floating in a concrete mixture inside a truck; and determining a property of the concrete mixture, based on the data received from the device.

Suitably, the data comprises an indicator of a motion of the device, and the method further comprises:

determining a slump of the concrete mixture, based on the data.

Suitably, the data comprises one of a temperature measurement, a pH measurement, an inductance measurement, an impedance measurement, a resistivity measurement, a sonic measurement, a conductivity measure, a pressure measurement, and an elevation measurement.

In accordance with another embodiment, a method of manufacturing a measuring device can be defined as comprising:

softening a selected material;

pressing the softened material into a mold to form a first hemisphere;

depositing sensors into the first hemisphere;

joining a second hemisphere to the first hemisphere to form a sphere;

sealing a connection between the second hemisphere and the first hemisphere; and injecting a selected gas into the sphere.

Suitably, the selected material comprises one of a metal, a plastic resin, and a polymer.

Suitably, the selected gas comprises nitrogen.

In accordance with an embodiment, a sensing device includes a shell comprising an elastomeric material, the shell including a first portion having a first end and a second portion having a second end. The shell may be egg-shaped or another shape. The first portion includes a thermally and electrically conducting disc, and a plate attached to the disc, the plate including a temperature sensor, a location sensor, and a micro-fiber composite sensor adapted to generate a measure of deformation, and an antenna, and a first electrode attached to the disc, the electrode extending through a first hole in the first portion of the shell. The second portion includes a predetermined quantity of a selected metallic substance embedded on the inside surface of an end of the second portion, and a second electrode connected to the metallic substance, the second electrode extending through a second hole in the second portion of the shell.

On another embodiment, the plate further includes one of an impedance/conductivity sensor, a pH sensor, an accelerometer, an elevation sensor, a RFID device, and a humidity sensor.

In another embodiment, the selected metallic substance comprises one of copper and brass.

In another embodiment, the thermally and electrically conducting disc is disposed perpendicular to an axis of the sensing device.

In another embodiment, the plate is perpendicular to the thermally and electrically conducting disc.

In accordance with another embodiment, a plurality of sensing devices are inserted into a concrete mixture at a production facility, first data is received from the plurality of sensing devices while the plurality of sensing devices are in the concrete mixture at the production facility, second data is received from the plurality of sensing devices while the plurality of sensing devices are in the concrete mixture in a vehicle transporting the concrete mixture to a construction site, third data is received from the plurality of sensing devices while the plurality of sensing devices are in the concrete mixture after the concrete mixture has been laid at a construction site, the first, second and third data are stored in a memory, and a prediction of a characteristic of the concrete mixture is generated based on the first, second and third data.

In one embodiment, the method also includes causing the concrete mixture and the plurality of sensing devices to be transported on a vehicle.

In another embodiment, the characteristic includes one of concrete strength and slump.

In another embodiment, fourth data representing a deformation is received from the MFC sensor, and an estimate of a slump of the concrete mixture is determined based on the fourth data.

In accordance with another embodiment, a method of managing a closed-loop production and delivery system is provided. An order for a product is received, wherein the order defines a formulation that specifies a plurality of components of the product and a quantity of sensing devices. In response to the order, the product is produced based on the formulation. The specified quantity of sensing devices are inserted into the product. Data is received from the sensing devices at one or more stages of production and delivery. A characteristic of the product is determined based on the data.

In one embodiment, the product is a concrete mixture.

In another embodiment, each sensing devices includes an egg shaped sensing device that includes a temperature sensor and an antenna.

In another embodiment, the characteristic includes one of concrete strength and slump.

In another embodiment, the product is one of a food products, a paint product, a petroleum-based product, and a chemical product.

BRIEF DESCRIPTION OF THE DRAWINGS

These and other aspects of the present Invention will be more fully understood by reference to one of the following drawings.

FIG. 14B shows a plurality of sensing devices disposed in a concrete mixture while the mixture is in a drum of a mixing truck in accordance with an embodiment;

DETAILED DESCRIPTION OF THE INVENTION

Figure 1:
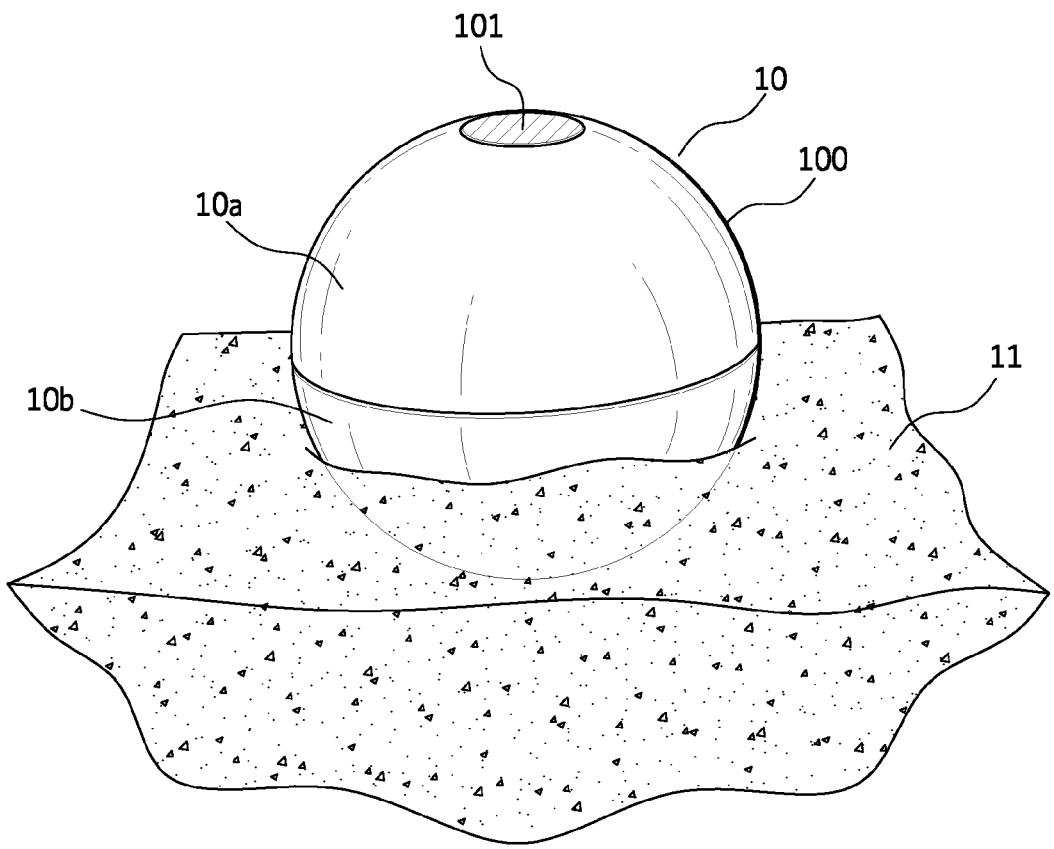
FIG. 1 is a perspective view of one embodiment of the floating wireless measuring device in accordance with an embodiment.

FIG. 1 shows a perspective view of one embodiment of a floating wireless measuring device 10. The floating wireless measuring device 10 in FIG. 1 is illustrated having a shell 100 and a transmitter 101. In FIG. 1, the floating wireless measuring device 10 floats at the surface of a fluid concrete 11 because the device 10 has a weight less than a buoyancy of the device 10.

When the device 10 floats at the surface of the fluid concrete 11, at least a part of an upper half 10a is above the surface of the concrete 11. Preferably, the transmitter 101 is placed in the upper half 10a of the device 10 above the surface of the concrete 11. The upper half 10a of the device 10 can be lighter than a lower surface 10b to stabilize the device 10 at the surface of the concrete 11.

The shell 100 can have any suitable diameter. Preferably, the diameter of the shell 100 is smaller than the diameter of an outlet of a drum of a concrete mixer truck. For example, the diameter of the shell 100 can be between about 1 cm and 10 cm, preferably about 3 cm and 8 cm, or more preferably about 4 cm and 6 cm. Alternatively, the diameter of the shell 100 can be at most about 5 cm, for example between about 3 cm and 5 cm.

The shell 100 can be made of any suitable material which can survive agitations of a concrete mixer truck and pumping of a fluid concrete or pouring the fluid concrete into structure by conventional methods. Preferably, the shell 100 is made of at least one of a metal such as steel, stainless steel, titanium, or aluminum; a plastic resin such as a tough plastic resin or a reinforced plastic resin; or any combination thereof.

The shell 100 can additionally include a foam resin layer. The form resin layer can be made of any appropriate polymer such as polystyrene. The foam resin layer can cover the entire surface of the shell 100, but alternatively the foam resin layer can partially cover the shell 100. For example, the foam resin layer can cover only the upper half 10a of the device 10. The foam resin layer can be formed to protect the device 10 from an impact or help the device 10 float at the surface of the fluid concrete.

Although the floating wireless measuring device 10 is illustrated having the spherical shape, the device 10 can be any suitable shape to be floated at the surface of the fluid concrete 11. Accordingly, the device 10 can be polyhedral, for example, cubic.

Figure 2:
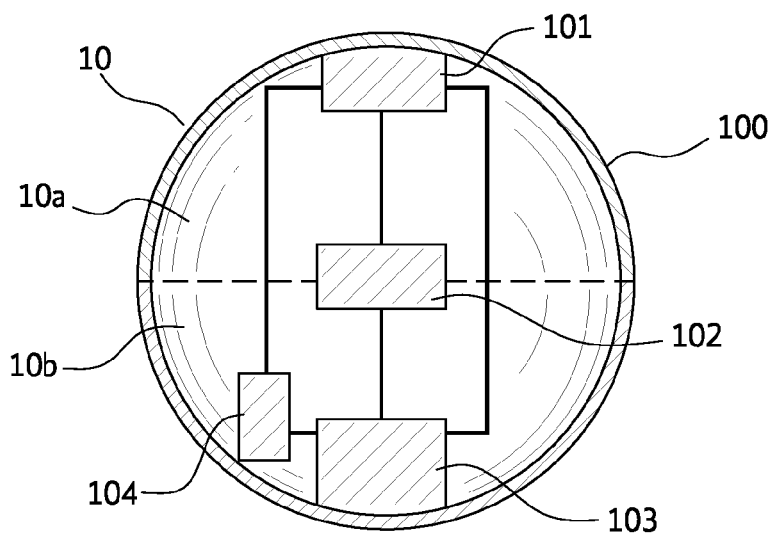
FIG. 2 is a cross-section view of one embodiment of the floating wireless measuring device in accordance with an embodiment.

FIG. 2 shows an embodiment of a vertical cross-section view of the floating wireless measuring device 10 illustrated in FIG. 1. The floating wireless measuring device 10 includes a sensor 103 for measuring a property of a fluid concrete, a transmitter 101 connected to the sensor 103 for transmitting data from the sensor 103, a power source 102 connected to the sensor 103 and the transmitter 101, and an additional component 104 connected to the transmitter 101, the sensor 103 and the power source 102.

The sensor 103 can be any kind of sensors that can be installed inside the shell 100 and measure a property of a fluid concrete. For example, the sensor 103 can be at least one of a temperature sensor, an accelerometer, a pH sensor, an inductance sensor, an impedance or resistivity sensor, a sonic sensor, a pressure sensor, a conductivity sensor, or an elevation sensor. One example of the temperature sensor is a miniature-sized temperature logger "SMARTBUTTON" (ACR SYSTEMS INC.).

Concrete's temperature measured by the temperature sensor can be converted to maturity and real time concrete setting and strength estimation in combination with real time data relating to mixture proportions, and materials items batched, and by reference to calibration data in a central database. The accelerometer can inform of whether the device 10 is in motion or stationary. The elevation sensor can inform how high the device 10 is elevated after a fluid concrete is poured at a construction site. The inductance sensor and the impedance or resistivity sensor can give data about the strength and setting, as well as its water-cement ratio. For example, before a fluid concrete sets, the pores of the concrete are full of water with electrolytes such as Na, K, Ca, and the like rendering the pure solution conducting and thus appearing as a secondary coil. The measurements by these sensors can be used for in-situ reporting of mixture proportions.

The transmitter 101 can be any commercially-available transmitter which can be installed in the shell 100 and transmit data obtained from the sensor 103. For example, the transmitter 101 is a wireless chip for short distance transmission.

The transmitter 101 can be installed to an upper half 10a of the device 10, while the sensor 103 can be installed to a lower half 10b of the device 10. Preferably, at least a part of the upper half 10a is above the surface of a fluid concrete, while at least a part of the lower surface 10b of the device 10 contacts the fluid concrete. Accordingly, it is preferable that the sensor 103 is installed in the lower half 10b to measure a property of the fluid concrete, and the transmitter 101 is installed in the upper half 10a above the surface of the concrete to transmit data from the sensor 103.

The additional component 104 is, for example, a Global Positioning System (GPS) unit, a Radio Frequency Identification (RFID) tag, a time and date recorder, a data storage component, or any combination thereof. The additional component 104 can appropriately connect the transmitter 101, the power source 102, and the sensor 103. When two or more additional components are used, they can appropriately connect each other. However, it is possible that the additional component 104 is not included in the device 10.

The GPS unit can inform where the device 10 is during transporting a fluid concrete and when the concrete is poured at a construction site. The RFID tag can be read by a tag reader. The RFID tag can be another way of tracking concrete pours and the location of each pour. RFID tags may be used to uniquely link and identify each device 10 with a batch ticket associated with a truck load, for example. Thus, the device may be linked to its mix parent and physical batch result within a closed loop production system.

The location of the additional component 104 inside the shell 100 can be appropriately decided. Whether the additional component 104 is placed in the upper half 10a or the lower half 10b of the device 10 can be suitably decided.

The transmitter 101, the power source 102, the sensor 103, and the additional component 104 can be connected by any known means.

Figure 3:
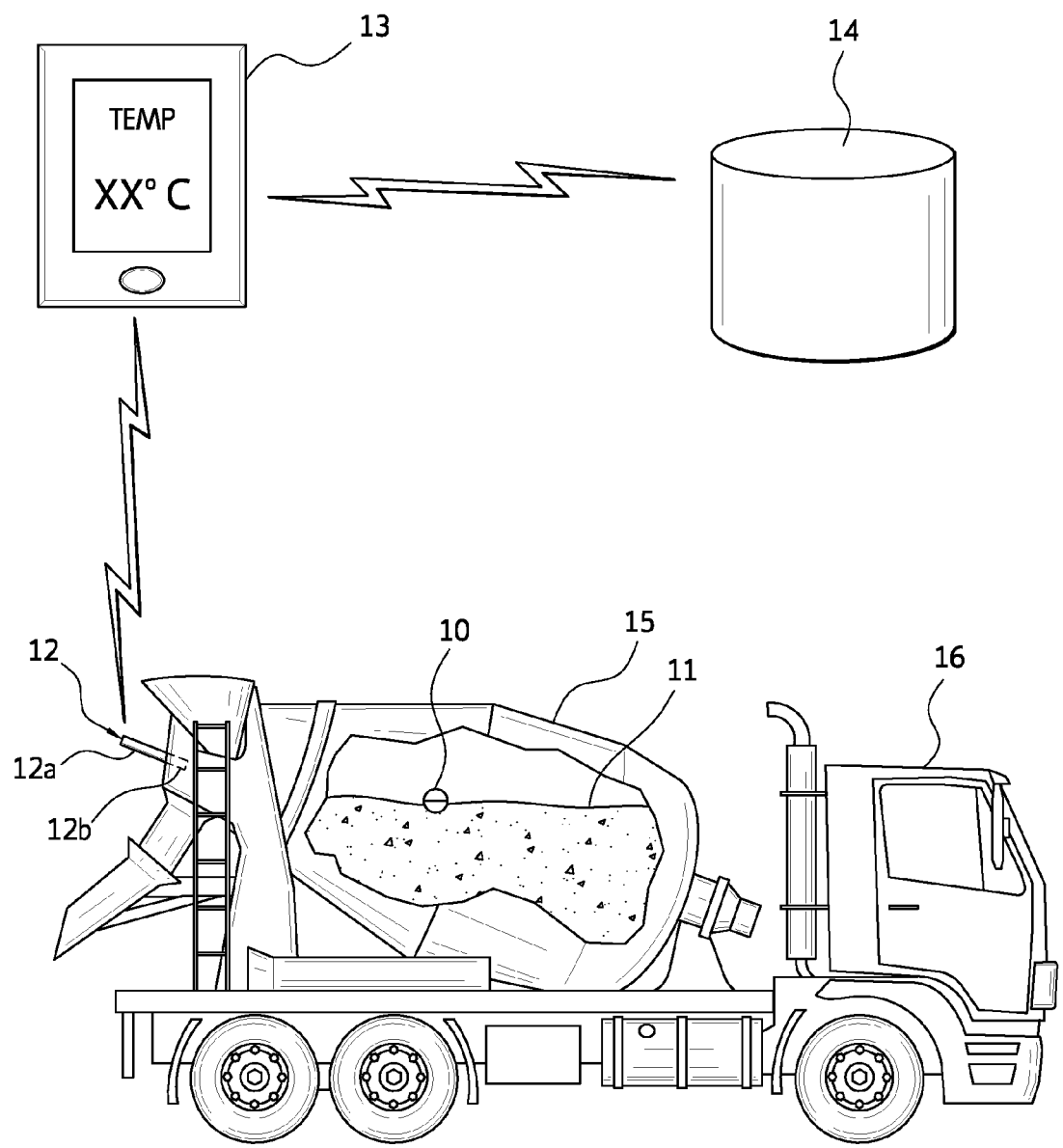
FIG. 3 is an overview of one embodiment of the system for measuring a property of a fluid concrete in a mixer truck in accordance with an embodiment.

FIG. 3 shows a system for measuring a property of a fluid concrete 11 in a mixer truck 16. The system includes the floating wireless measuring device 10 and an antenna 12 mounted in a side of a drum 15 of the mixer truck 16. The antenna 21 transmits data from the device 10 inside the drum 15 to outside the drum 15.

The device 10 can be put in the drum 15 before or at batching time, or after the truck 16 is loaded with the fluid concrete 16. For example, the device 10 can be shot into the drum 15 by a gun device. When the device 10 is shot into the truck at batching time, for example, an accelerometer in the device 10 can start a date and time recorder in the device 10 for measuring concrete age and recording when each type of measuring is transmitted.

When the fluid concrete 11 is not agitated in the drum 15, the device 10 floats at the surface of the concrete 11 and can transmit data.

The antenna 12 can comprise an outward looking wireless transmitter 12a and an inward looking wireless receiver 12b. The inward looking wireless receiver 12b can receive data from the device 10. The outward looking wireless transmitter 12a can transmit data from the device to a receiving device 13. The receiving device 13 can be a mobile device such as a cell phone. The receiving device 13 can send the data to a database 14. The database 14 can connect with the receiving device 13 with any know means such as a wireless connection.

The floating capability of the floating wireless measuring device 10 and the antenna 12 placed in a side of the drum 15 overcome the issues of not being able to transmit from within a conducting medium such as the fluid concrete 11 and the Faraday cage effect of the drum 15 of the mixer truck 16.

The method for measuring a property of a concrete will now be explained. As shown in FIG. 3, a property of the fluid concrete 11 in the mixer truck 16 can be measured by putting the wireless measuring device 10 in the drum 15 of the mixer truck 16; pouring the fluid concrete 11 into the drum 15 of the mixer truck 16; and correcting data for a property of the fluid concrete 11 by the wireless measuring device 10. This method can further include transmitting the data from the wireless measuring device 10; and receiving the data from the wireless measuring device 10. After pouring the fluid concrete 11 at a construction site, the device 10 can be poured with the concrete 11. The device 10 can measure in real time a property of the poured fluid concrete 11 during its hardening.

Advantageously, device 10 may be used to determine properties of the fluid concrete mixture while the concrete is inside of a truck. This capability may provide to a producer, or to a manager at a construction site, valuable information about the concrete prior to laying down the concrete.

Figure 4:
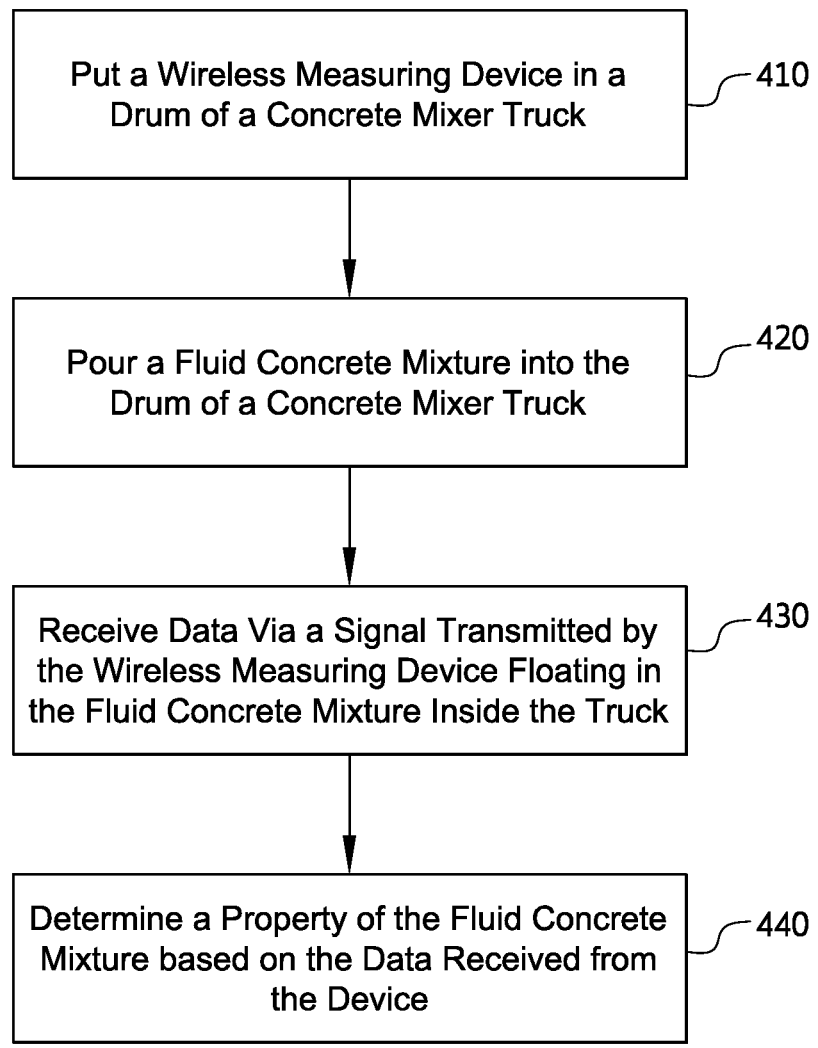
FIG. 4 is a flowchart of a method of determining a property of a concrete mixture in accordance with an embodiment.

For example, in an illustrative embodiment, device 10 may be used to determine a property, such as the slump, of a fluid concrete mixture while the concrete is inside of a truck. FIG. 4 is a flowchart of a method of determining a property of a fluid concrete mixture in accordance with an embodiment. At step 410, a wireless measuring device is put in a drum of a mixer truck. At step 420, a fluid concrete mixture is poured into the drum of the mixer truck. As described above, device 10 is put inside drum 15 of truck 16, and fluid concrete 11 is poured into the drum. As the drum 15 is agitated, the fluid concrete 11 moves and device 10 moves in the fluid concrete.

In other embodiments, dry components of concrete (instead of fluid concrete) are inserted into the drum of the mixer truck. Water is then added into the drum to produce fluid concrete. Device 10 may be added into the drum at any time during this process. Device 10 may be added to dry components of concrete or to fluid concrete.

In the illustrative embodiment, device 10 comprises an accelerometer and generates data indicating certain aspects of the device's motion. Device 10 may also include a GPS unit capable of generating location data. In other embodiments, other types of data, concerning various parameters relating to the device itself, or relating to the truck 16, or relating to the properties of the fluid concrete 11 inside the truck 16, may be obtained from a device floating in the fluid concrete 11 inside the truck 16.

At step 430, data is received via a signal transmitted by a device floating in a concrete mixture in a truck. In the illustrative embodiment, device 10 transmits signals containing motion data. The signals may also contain location data produced using the device's GPS capabilities. As described above, the signals are detected by antenna 12 and transmitted to receiving device 13 outside of the truck 16.

Device 13 receives the signals and extracts the motion data and location data from the signal. The motion data and location data may be stored in database 14, for example.

At step 440, a property of the concrete mixture is determined based on the data received from the device. In the illustrative embodiment, device 13 determines the slump of the fluid concrete 11 based on the motion data and location data received from device 10. The slump of a fluid concrete mixture may be determined from the motion data and location data using well-known methods.

In other embodiments, other properties of a fluid concrete mixture may be determined based on data received from device 10. For example, data from device 10 may be used to determine the water/cementitious ratio of a concrete mixture inside a truck.

In another embodiment, a plurality of devices similar to device 10 may be shot into drum 15, and float in the fluid concrete mixture inside the truck 16. Any number of devices may be shot into drum 15. In one embodiment, about one hundred (100) devices may be shot into the drum 15. When the concrete mixture is laid down at a construction site, the devices are allowed to remain in the mixture; the devices remain in the concrete as the concrete hardens, and thereafter. Each device continues to transmit data concerning various measurements as long as possible (e.g., until transmission is no longer possible or until the device's power source fails). For example, each device may transmit location data, temperature readings, pH measurements, inductance measurements, impedance measurements, resistivity measurements, sonic measurements, pressure measurements, conductivity measurements, elevation measurements, etc.

Figure 5:
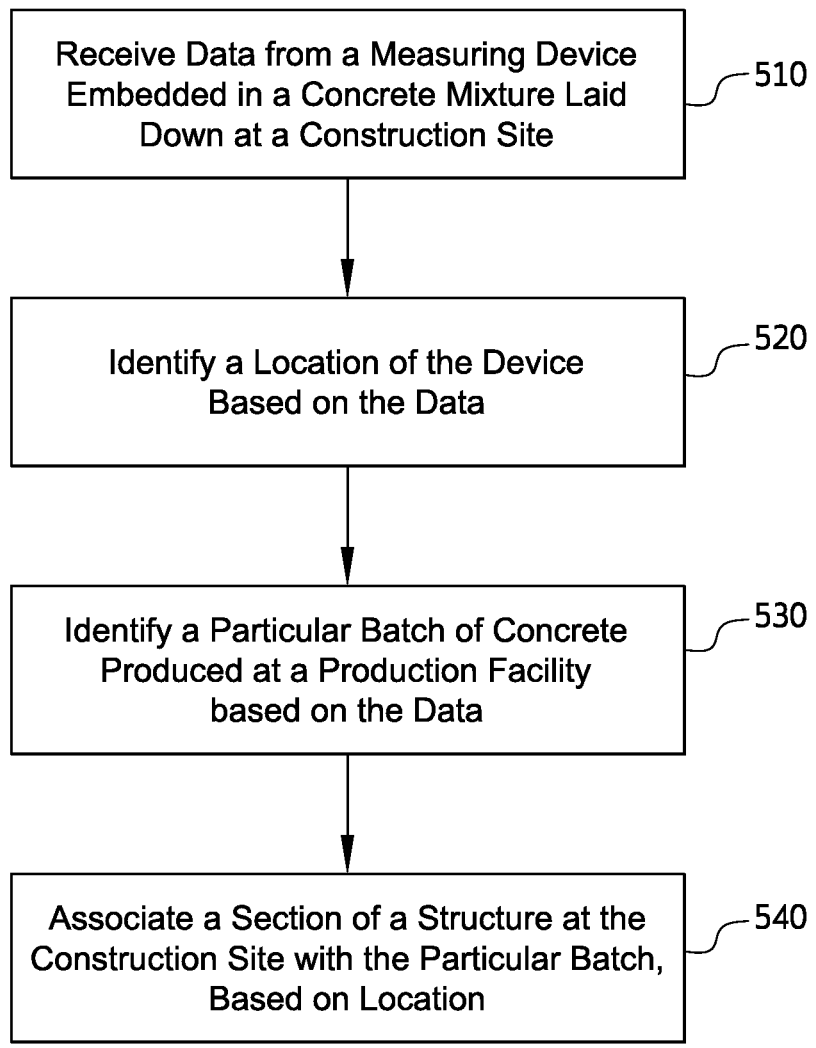
FIG. 5 is a flowchart of a method of associating a batch of a fluid concrete mixture with a section of a structure at a construction site in accordance with an embodiment.

FIG. 5 is a flowchart of a method in accordance with an embodiment. Suppose, in an illustrative example, that a plurality of devices (such as device 10) are shot into drum 15 and subsequently remain in the fluid concrete 11 as the concrete is laid down. Suppose further that the construction project requires ten truckloads of concrete. For convenience, in this example, each truckload represents one batch. Data received from the devices may be used to keep track of where each respective batch is laid. Thus, at step 510, data is received from a measuring device embedded in a concrete mixture laid down at a construction site. Data including location data, elevation data, etc., is received from one or more devices embedded in the concrete that has been laid down. At step 520, a location of the device is identified based on the data. The location data from a particular device may indicate that the device is located in a particular section of a parking lot, for example. At step 530, a particular batch of concrete produced at a production facility is identified based on the data. The device may provide identifying information from which it may be determined which truck the device was in. For example, each device may transmit a unique identifier. Knowledge of which truck the device was in may be used to determine the batch of concrete that the device is in. At step 540, a section of a structure at the construction site is associated with the particular batch, based on the location; for example, a linkage may be established between an RFID tag of a device and the batch when the device is introduced into concrete at the production facility, discharge chute or pump, or manually thrown into a structural element. The batch of concrete may then be associated with the identified section of the structure at the construction site (e.g., the section of the parking lot). Data associating respective batches with respective locations at a construction site may be stored for future use.

Using a plurality of devices in this manner advantageously enables a producer, or the manager of the construction site, to monitor the progress of a construction project. Leaving one or more devices in the concrete at the worksite also advantageously enables a producer or site manager to monitor when and where each particular batch or truckload of concrete is laid down. Possession of such information may enable a producer to monitor the performance of each batch of concrete produced, and thereby to achieve better control over the quality of the final product.

In another embodiment, a device similar to device 10 may store measurement data in a memory within the device without transmitting the data. The device may be retrieved at a later time, for example, when the concrete mixture is laid down, and the data retrieved from the device's memory.

Figure 6:
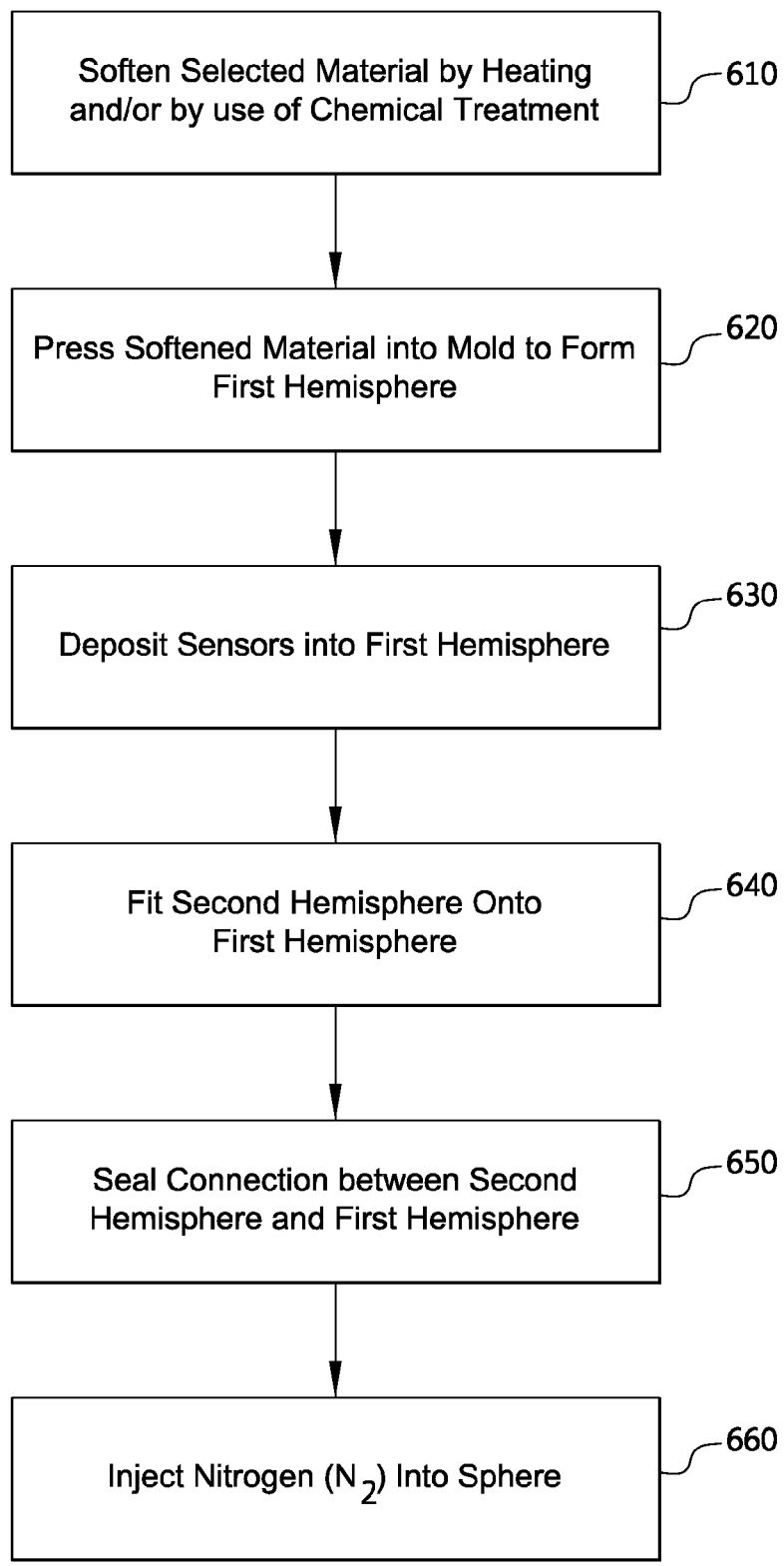
FIG. 6 is a flowchart of a method of manufacturing a measuring device in accordance with an embodiment.

In accordance with another embodiment, a method of manufacturing a measuring device such as device 10 is provided. FIG. 6 is a flowchart of a method of manufacturing a measuring device in accordance with an embodiment. At step 610, a selected material is softened by heating and/or by use of chemical treatment. For example, in an embodiment in which a polystyrene material is used, the polystyrene is heated, causing the material to soften.

Figure 7:
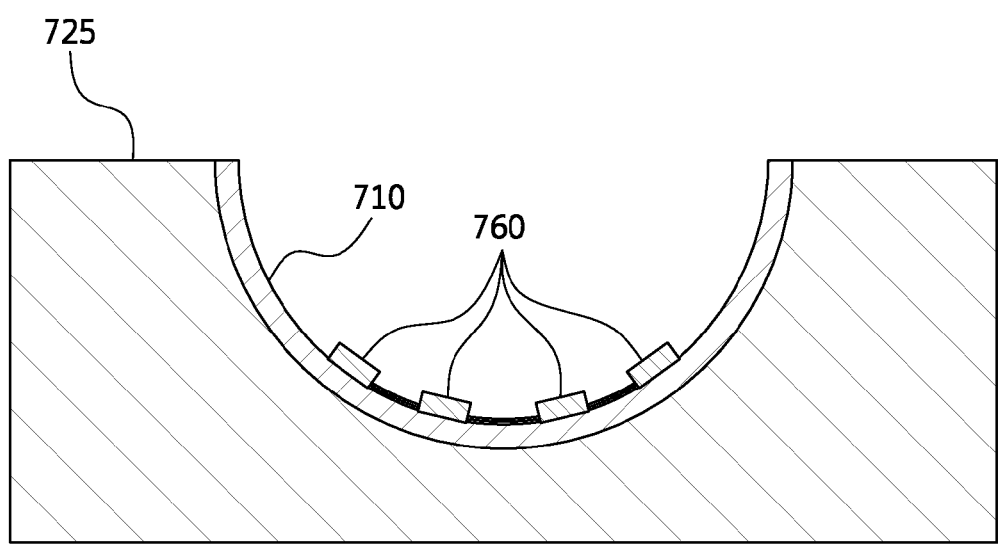
FIG. 7 shows a cross section of a mold in which a softened material has been pressed in accordance with an embodiment.

At step 620, the softened material is pressed into a mold to form a first hemisphere. FIG. 7 shows a cross section of a mold 725 in which a softened material 710 has been pressed in accordance with an embodiment. The mold forms a hemispherical shape.

At step 630, sensors are deposited into the first hemisphere. In the illustrative embodiment of FIG. 7, sensors 760 are embedded in the exposed internal surface of softened material layer 710, while the material is in the mold.

Figure 8A:
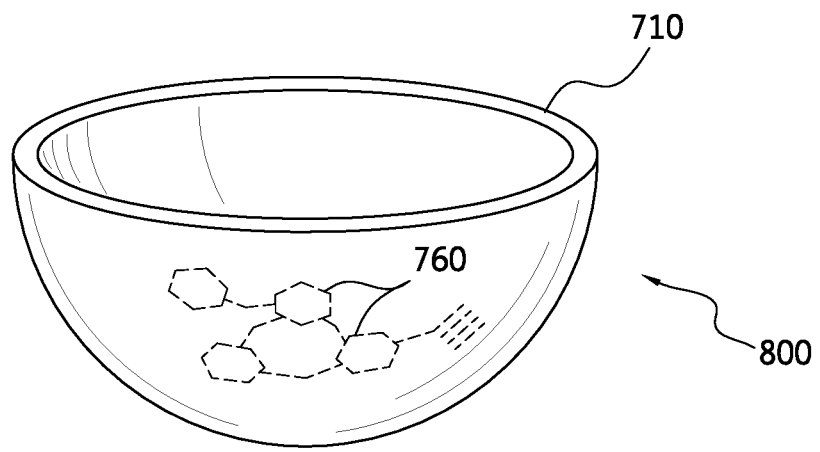
FIGS. 8A-8B show a side view and a top view, respectively, of a hemisphere formed of a material layer, after removal from a mold in accordance with an embodiment.
Figure 8B:
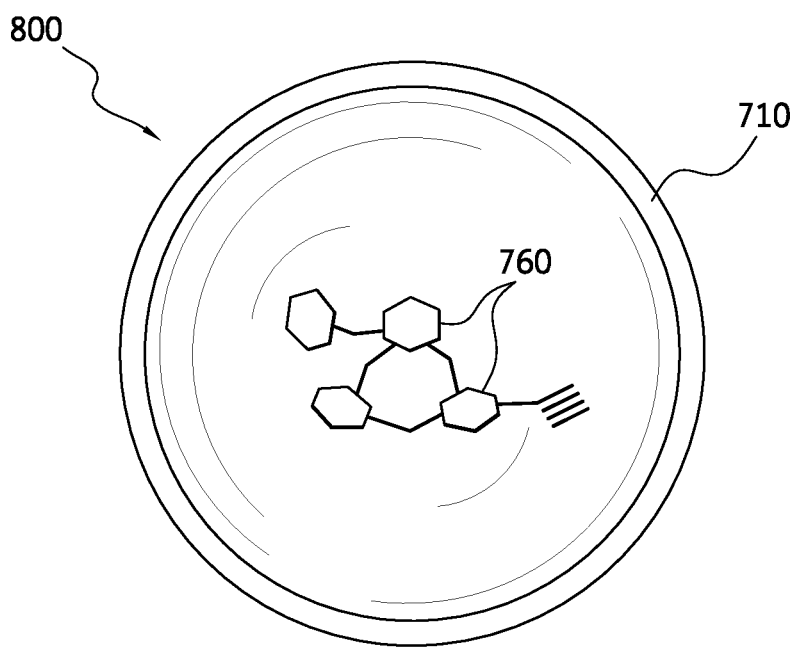

After the material hardens, the hemisphere may be removed from mold 725. FIGS. 8A-8B show a side view and a top view, respectively, of a hemisphere 800 formed of material layer 710, after removal from mold 725 in accordance with an embodiment. Sensors 760 are embedded on the inside surface of hemisphere 800.

Figure 9:
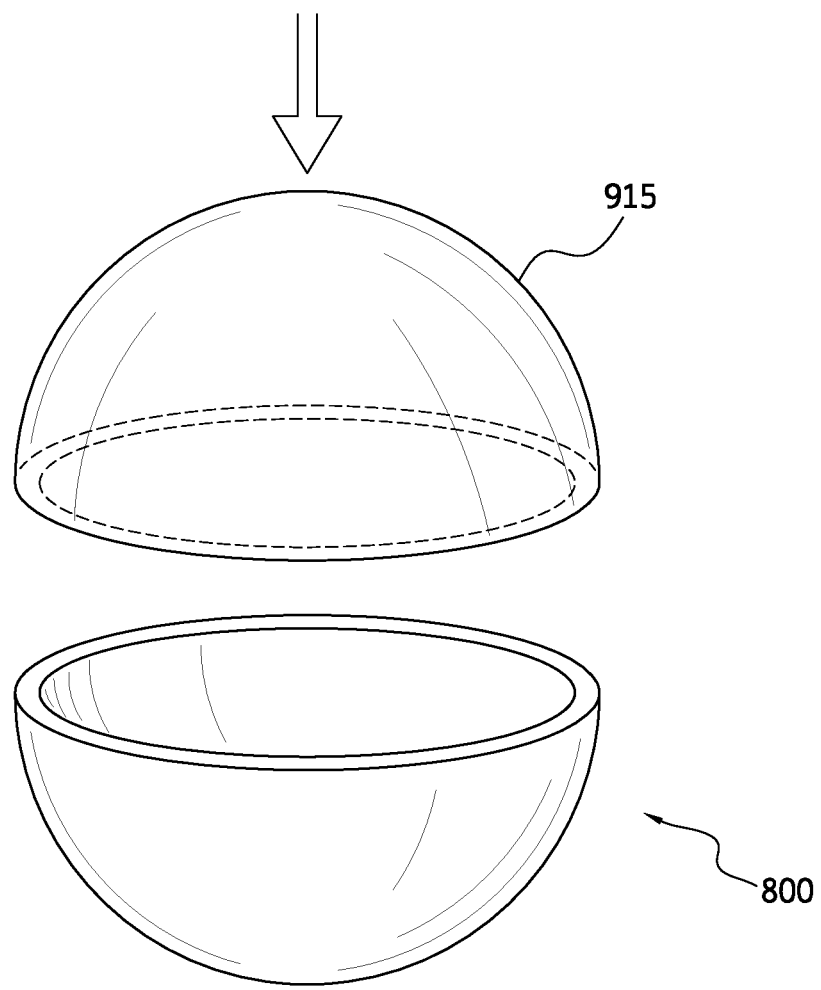
FIG. 9 shows a second hemisphere attached to a first hemisphere in accordance with an embodiment.
Figure 10:
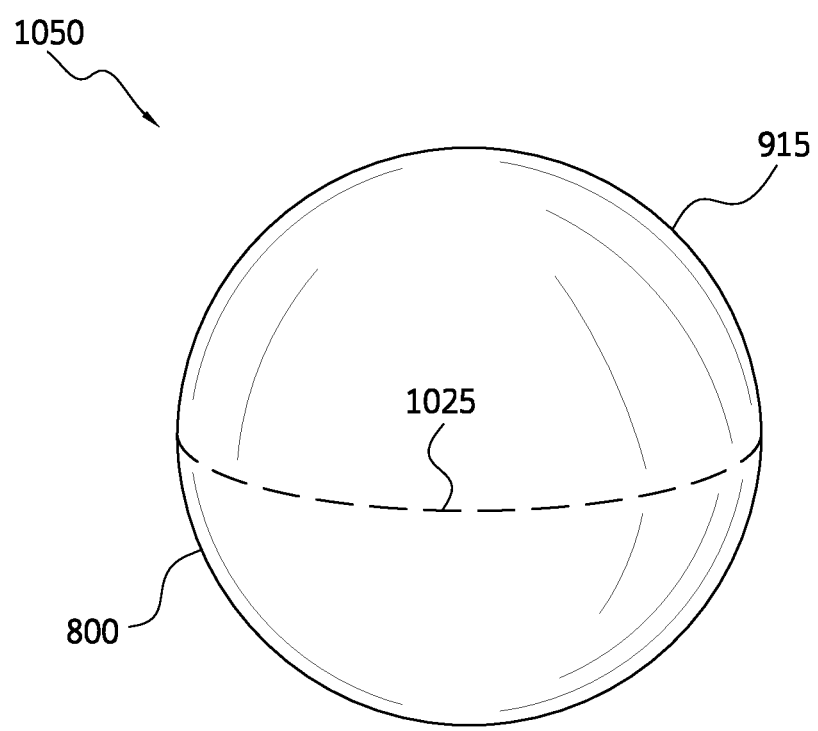
FIG. 10 shows a sphere comprising a first hemisphere, a second hemisphere, and a connection in accordance with an embodiment.

At step 640, a second hemisphere is fitted onto the first hemisphere, creating a sphere. In an illustrative embodiment shown in FIGS. 9-10, a second hemisphere 915 is fitted onto first hemisphere 800, forming a shell 1050 which is in the form of a sphere. Second hemisphere 915 may a hemisphere manufactured in a manner similar to that described above; however, second hemisphere 915 may, or may not, comprise sensors. Hemispheres 800 and 915 are joined at a connection 1025.

At step 650, the connection between the first hemisphere and the second hemisphere is sealed. In the illustrative embodiment, connection 1025 is sealed, for example, by using an appropriate glue.

At step 660, nitrogen ($N_2$) is injected into the sphere. Known techniques may be used to pump nitrogen into spherical shell 1050. In other embodiments, other gases may be used.

Figure 11:
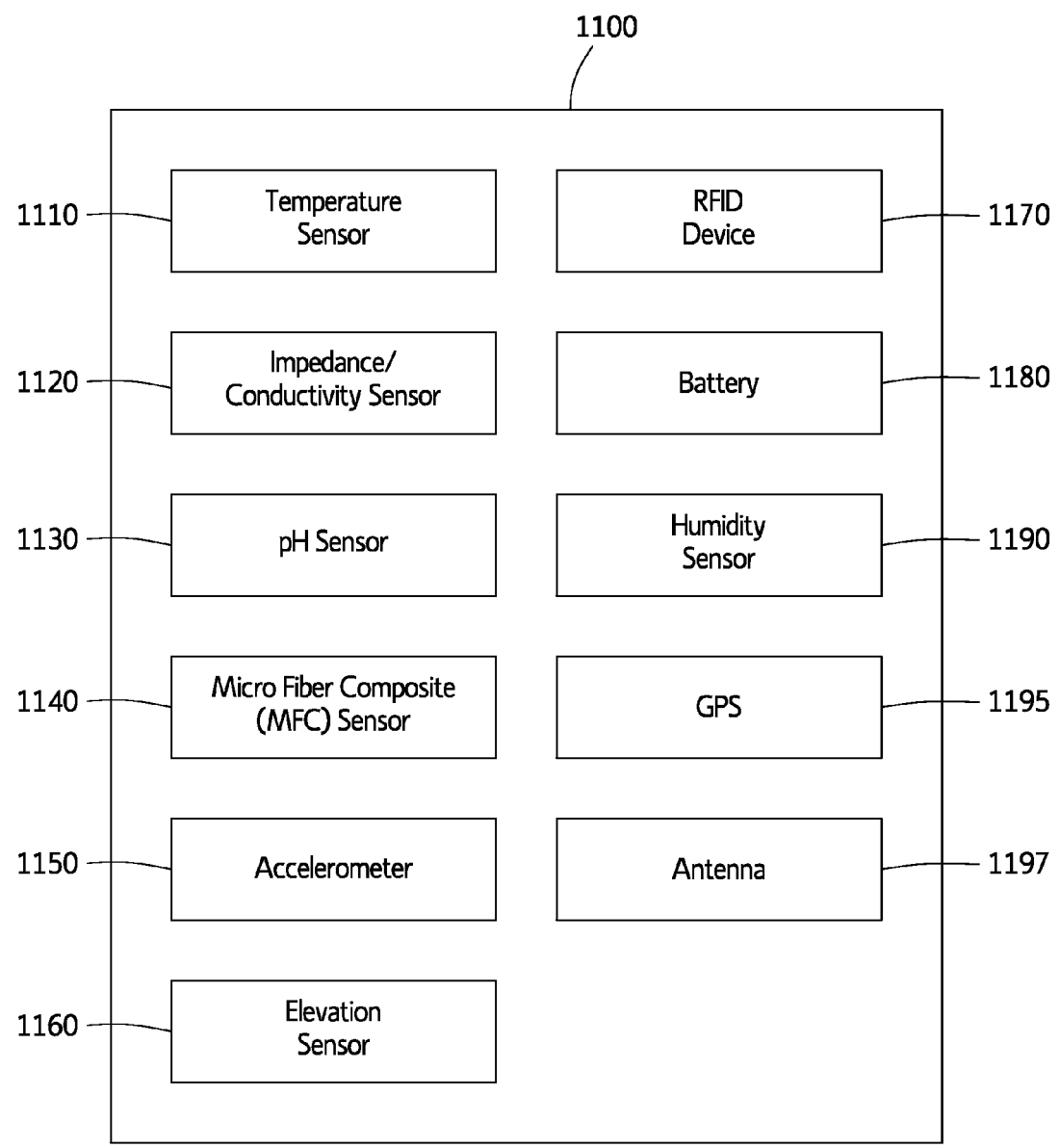
FIG. 11 shows components of a sensing device in accordance with another embodiment.

FIG. 11 shows components of a sensing device in accordance with another embodiment. Sensing device 1100 includes a temperature sensor 1110, an impedance/conductivity sensor 1120, a pH sensor 1130, a micro fiber composite (MFC) sensor 1140, an accelerometer 1150, an elevation sensor 1160, a radio frequency identification (RFID) device 1170, a battery 1180, a humidity sensor 1190, a GPS-based geolocation sensor 1195, and an antenna 1197.

Temperature sensor 1110 detects the temperature of a concrete mixture or of another fluid in which the sensing device is floating. Temperature information can be used to analyze concrete maturity. For example, curing rate temperature dependency may be analyzed using the ASTM C74 method. In-place, in-structure strength may be estimated probabilistically as a function of curing age. Because concrete gains strength by maturity, it is valuable to builders to be able determine its curing age at a standard reference temperature.

Impedance/conductivity sensor 1120 measures the impedance and conductivity of concrete. Impedance and conductivity measurements may be used to determine real-time strength estimates, for example. Real-time strength estimates may be corrected for unrecorded water additions on the basis of real-time conductivity measurements. Conductivity of a concrete mixture decreases with age and correlates with the degree of hydration. DC conductivity may be measured. Alternatively, AC conductivity may be measured.

pH sensor 1130 measures the pH of a concrete mixture. pH measurements may capture unexpected overly retarded or accelerated setting due to concrete/chemical admix mismatches. pH measurements may be used in estimating concrete setting behavior, placeability, and pumpability performance.

Micro fiber composite (MFC) sensor 1140 measures a cumulative deformational voltage. MFC sensor 1140 may include a piezoelectric substance that generates a voltage when strained, for example. As MFC sensor 1140 is deformed, a voltage is generated indicating the degree of deformation. This voltage information may be used to determine a degree of concrete agitation, a measure of viscous drag forces experienced by sensor device 1100, for example. Such information may be used to determine characteristics of the concrete mixture, for example, estimates of mixing energy, slump, etc. Such information may be used in conjunction with data obtained by accelerometer 1150 to determine characteristics of the concrete mixture such as slump, mixing energy, etc.

MFC sensor 1140 may be calibrated for concrete based on, for example, measurements in water.

Accelerometer 1150 obtains data relating to the motion of sensing device 1100. For example, accelerometer 1150 may measure a degree of acceleration due to mixing of concrete in a truck, transport of the concrete, and placement of the concrete. Accelerometer 1150 may measure non-steady motion, a degree of fluid drag resisting motion as compared to water, etc. Data from accelerometer 1150 may be used to determine a measure of slump, flowability, etc. For example, in a spinning tank containing concrete having a high water content, accelerometer 1150 may indicate a relatively low drag; in a spinning tank containing concrete having a low water content, accelerometer 1150 may indicate a high drag.

Elevation sensor 1160 detects the elevation of sensing device 1100. For example, this may allow an operator to determine where the sensing device is located in a structure after the concrete has been poured. In some embodiments, a large number of sensing devices may be distributed throughout the poured concrete and, consequently, sensing devices may be distributed throughout different locations and different levels of the structure being constructed. An operator may continue to receive data from each of the sensing devices and use the data to monitor the drying and performance of the concrete.

RFID device 1170 transmits a signal containing one or more identifiers. The identifier may be associated with a batch, a mixture, a structure, a project, etc. The identifier may include a pod serial number, for example. The identifier may be used to link data generated by the sensing device during manufacturing, transportation, placement, and data generated while in the structure to a specific batch, mixture, project, etc. As a result, each sensing device may have access to other data already obtained and stored in a closed-loop system database, such as batched performance specifications such as slump, strength, batched materials contents such as water, cementitious, water/cm ratio, expected strength at point of delivery if lab cured at 20 dC, etc.

In one embodiment, sensing device 1100 transmits location coordinates and its RFID serial number or identifier. Each sensing device has a unique RFID serial number/identifier. When a sensing device is inserted into a concrete mixture, a batch ticket associated with the concrete batch is linked in a one-to-one relationship to the RFID serial number.

Battery 1180 may be any suitable battery or other type of power device. Battery 1180 may be a watch-type battery, for example.

Humidity sensor 1190 measures the humidity of a concrete mixture. Humidity sensor 1190 may measure concrete pore humidity, for example. In many instances, concrete needs close to 100% humidity to cure and develop strength. When humidity drops below 80% concrete curing and hydration may cease. In-place concrete strength may be modeled by delivering probable strength as a baseline, analyzing historical humidity and temperature measurements from sensing device 1100, etc. Delivered probable strength as a baseline may be corrected for on-location water additions using conductivity measurements.

GPS based geolocation sensor 1195 uses GPS measurements to detect the location of sensing device 1100. Location measurements may be used to determine where the sensing device is located and thus be used to determine where concrete-related activities such as transportation, pouring, etc., occur.

Antenna 1197 transmits data, and may receive data. Antenna 1197 may be Bluetooth and/or Wi Fi capable. Antenna 1197 may be integrated with GPS sensor 1195.

Figure 12:
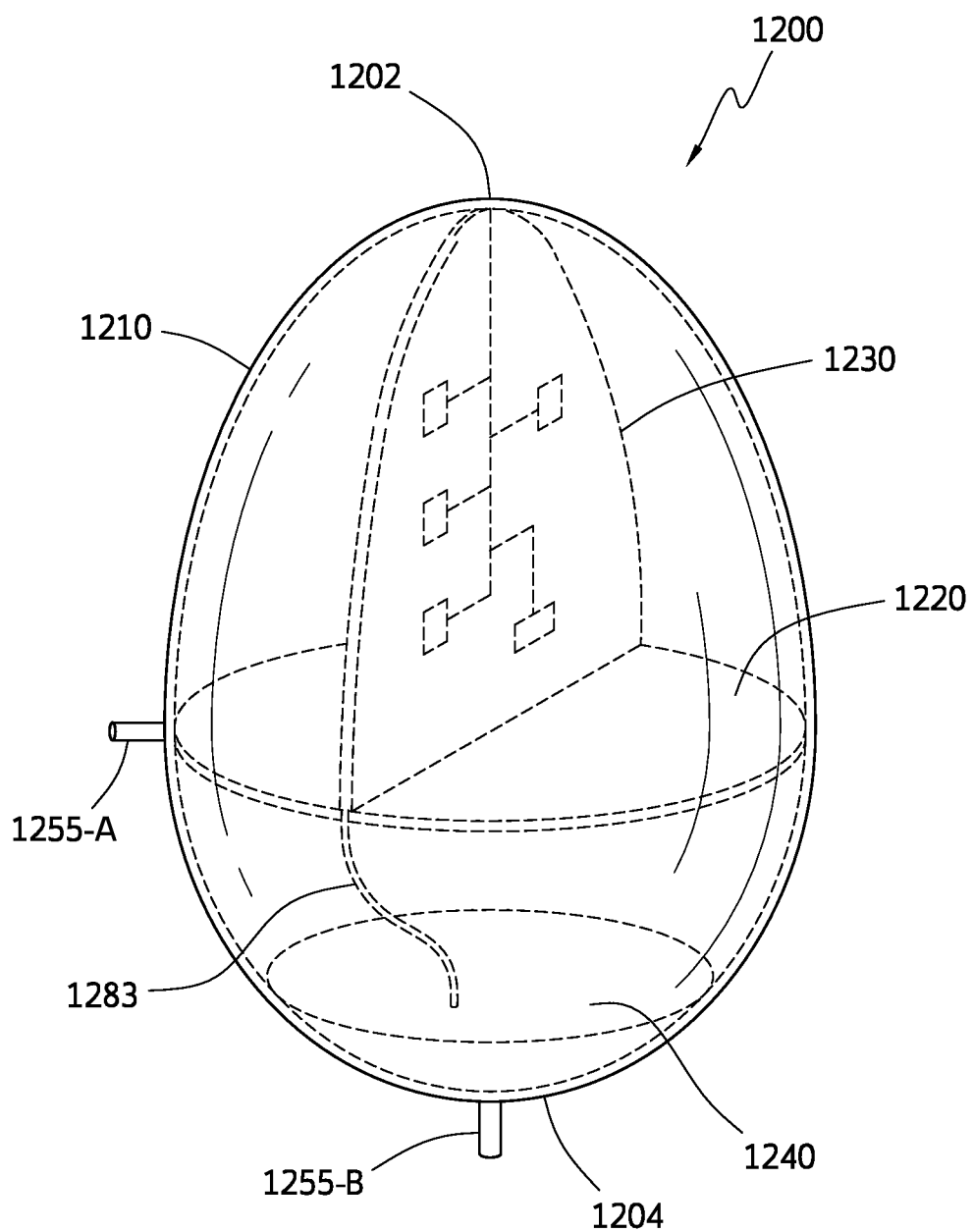
FIG. 12 shows a sensing device in accordance with an embodiment.

FIG. 12 shows a sensing device 1200 in accordance with an embodiment. Sensing device 1200 includes a shell 1210. Shell 1210 has an egg shape and includes a narrower end 1202 and a flatter end 1204. In other embodiments, shell 1210 may have a different shape. Shell 1210 is made of an elastomeric material such as silicone rubber, neoprene, a thermoplastic elastomer, or a similar material. Shell 1210 may be approximately 2-3 mm thick, for example, and have an aspect ratio between about 1.4 to 2.0, for example. The diameter of shell 1210 may be between about 0.10 inch and 2.0 inch, for example. The height of shell 1210 may be between about 0.25 inch and 3.0 inches, for example.

Sensing device 1200 has a low center of gravity. Sensing device 1200 has an effective specific gravity between about 0.9 to 1.5.

Sensing device 1200 may be pressurized with nitrogen gas at about 2-3 atmospheres.

Sensing device 1200 includes a disc 1220, which provides structure. Disc 1220 may function as a thermally and electrically conducting disc. Disc 1220 may therefore function as a temperature measuring disc. Disc 1220 is a circular disc disposed perpendicular to the axis of the sensing device (the axis being defined as the line between the narrower end 1202 and the flatter end 1204).

Sensing device 1200 also includes a metallic and electrically conducting substance 1240 at the flatter end 1204 to provide a weight at the flatter end 1204; the additional weight causes sensing device 1200 to float with an orientation such that the narrower end 1202 remains above the water-line or fluid-line while the flatter end 1204 remains submerged. Substance 1240 may be embedded in the inside surface of shell 1210 at the flatter end 1204, or otherwise attached to the inside surface of shell 1210 at flatter end 1204. Substance 1240 may include a predetermined amount of a metallic and conducting substance, for example. Substance 1240 may be copper or brass, for example. The end of sensing device 1200 with flatter end 1204 is heavier than the end of sensing device 1200 with narrower end 1020. Substance 1240 weighs down the flatter end 1204 for controlled buoyancy.

Due to the structure of sensing device 1200, and substance 1240 in particular, sensing device 1200 is buoyant and floats in liquid or fluid (such as fluid concrete) with flatter end 1204 submerged and narrower end 1202 remaining above the liquid/fluid. Narrower end 1202 remains "above water" while flatter end 1204 remains submerged.

Sensing device 1200 includes a first electrode 1255-A and a second electrode 1255-B. Electrode 1255-A includes a conductive material fitted through a hole in the side of shell 1210. Electrode 1255-A is connected to disc 1220. Second electrode 1255-B includes a conductive material fitted through a hole in shell 1210. Second electrode 1255-B is connected to substance 1240. First and second electrodes 1255-A, 1255-B may be used to obtain pH measurements, impedance measurements, conductivity measurements, measurements of dielectric properties, etc.

A wire 1283 or other conducting connection may connect substance 1240 to disc 1220.

Sensing device 1200 also includes a plate 1230. In the illustrative embodiment, plate 1230 is disposed perpendicular to disc 1220. Plate 1230 may include circuitry/electronics. Plate 1230 may include an integrated chip set, for example. Accordingly, plate 1230 may include electronics/circuitry to implement antenna 1197, for example and GPS-based location sensor 1195, for example. Plate 1230 may also include circuitry/electronics implementing all or a portion of one or more of the following components: temperature sensor 1110, impedance/conductivity sensor 1120, pH sensor 1130, micro fiber composite (MFC) sensor 1140, accelerometer 1150, elevation sensor 1160, radio frequency identification (RFID) device 1170, humidity sensor 1190, etc.

In some embodiments, plate 1230 may be plugged into disc 1220 to facilitate manufacturing of sensing device 1200.

Figure 13:
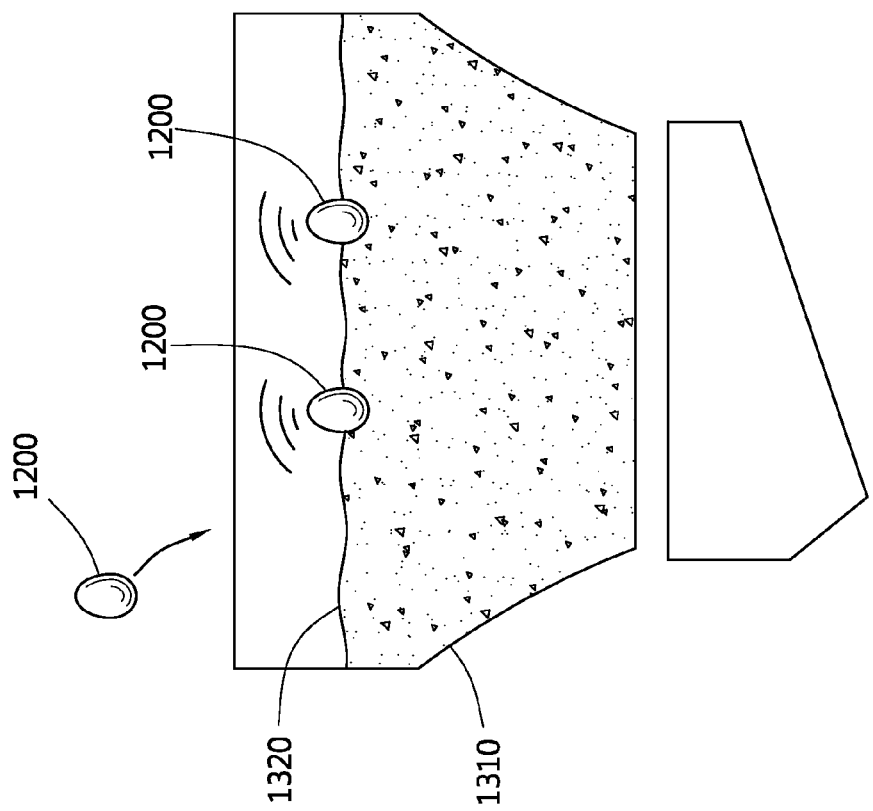
FIG. 13 shows a plurality of sensing devices disposed in a concrete mixture while the mixture is in a bin at a concrete production facility in accordance with an embodiment.
Figure 14A:
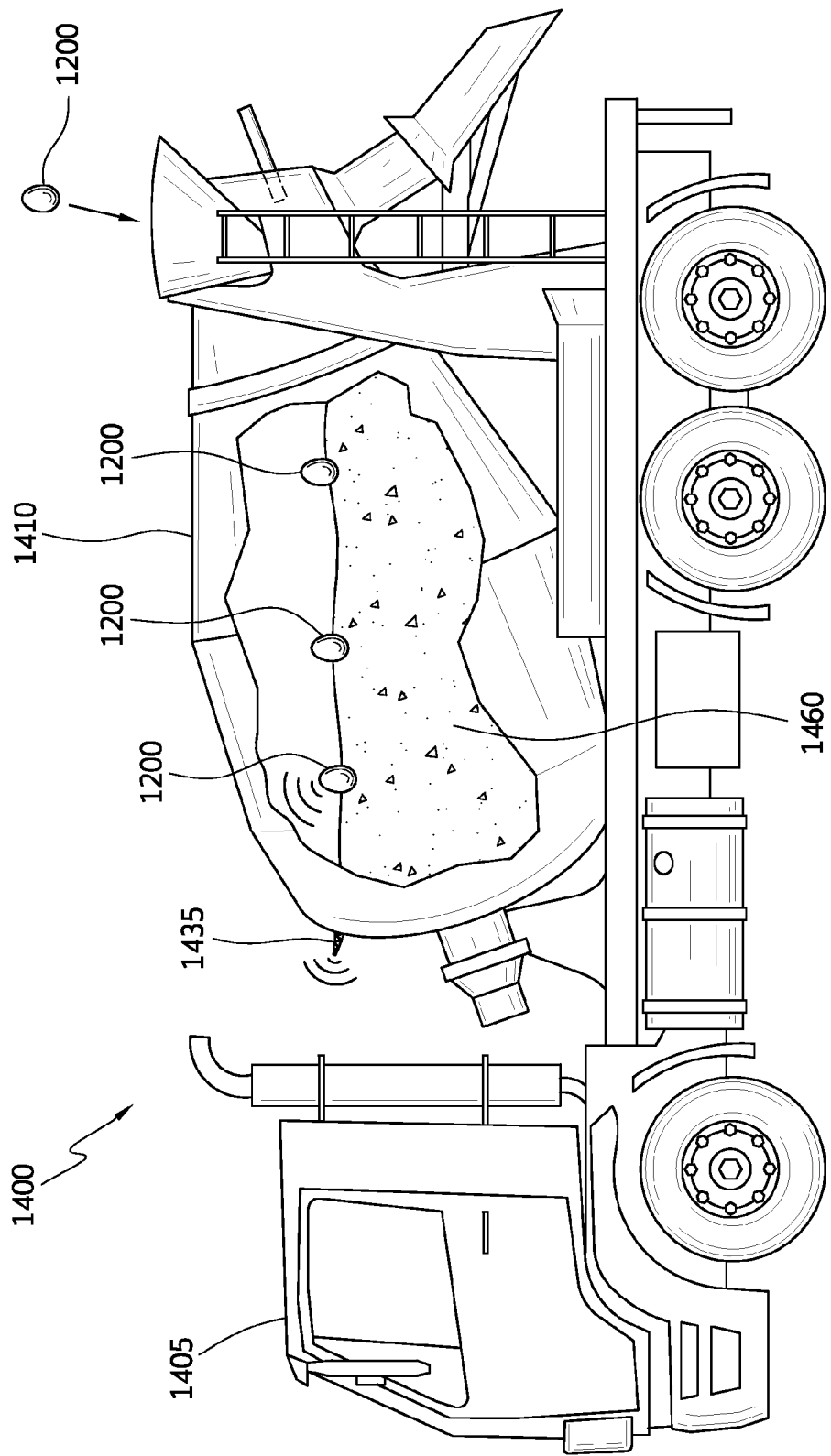
FIG. 14A shows a plurality of sensing devices disposed in a concrete mixture while the mixture is in a drum of a mixing truck in accordance with an embodiment.

One or more sensing devices such as sensing device 1100 or 1200 may be added to a concrete mixture at various stages of a manufacturing and delivery system. Referring to FIG. 13, in one embodiment, for example, one or more sensing devices 1200 may be added to a concrete mixture 1320 while the mixture is in a bin 1310 at a concrete production facility. Referring to FIG. 14A, in another embodiment, one or more sensing devices 1200 may be added to a concrete mixture 1460 while the mixture is in a drum 1410 of a concrete mixing truck 1400. In this illustrative example, an antenna 1435 is located on drum 1410. Antenna 1435 may include a Bluetooth antenna, for example. Antenna 1435 may receive signals from sensing devices 1200 which are disposed in the mixture 1460 within drum 1410.

Signals from antenna 1435 may be transmitted to a processing device (not shown) in the cab of truck 1400. For example, the driver of the truck may operate a laptop computer that receives the data from antenna 1435 and transmits it via the Internet (e.g., to master database module 1611 shown in FIG. 16).

FIG. 14B shows a view along an axis of drum 1410 as the drum spins. Concrete mixture 1460 spins within drum 1410. Sensing device(s) 1200 float within the concrete mixture. Sensing device(s) 1200 may spin around the inside of drum 1410 within the concrete due to centripetal and other forces. The narrow end of each sensing device 1200 remains above the fluid level of the concrete. Sensing device 1200 may transmit data from time to time; such data is received by antenna 1435 (which is located on drum 1410).

Figure 15:
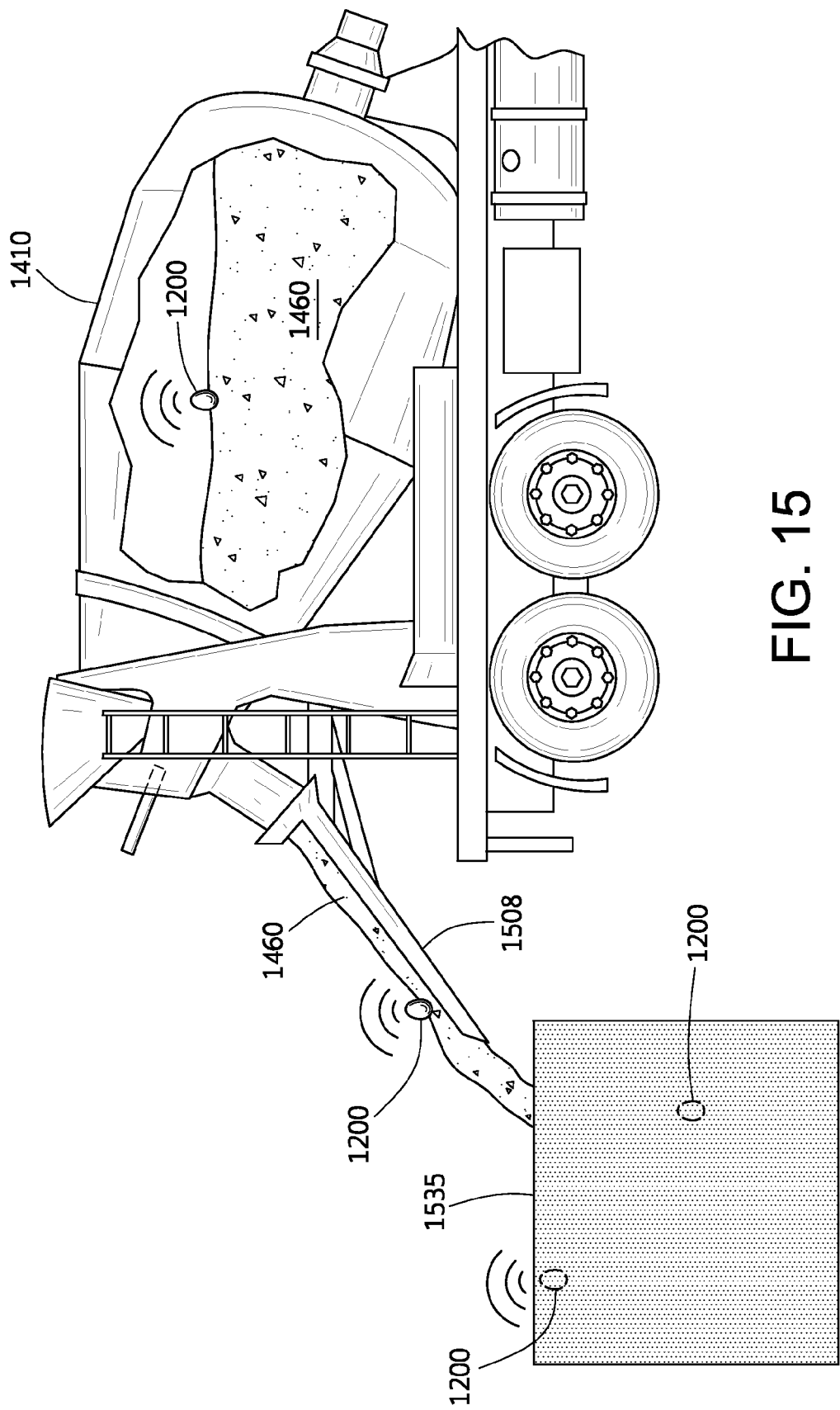
FIG. 15 shows a construction site in accordance with an embodiment.

FIG. 15 shows a construction site in accordance with an embodiment. The concrete mixture 1460 is poured along a chute 1508 from inside the drum 1410 of the truck. Concrete mixture 1460 is poured into a form to create a structure 1535. Sensing devices 1200 flow with the concrete mixture from the drum 1410 down along chute 1508 and into structure 1535. Sensing devices 1200 continue to transmit data from inside drum 1410, transmit data as the devices travel along chute 1508, and transmit data after placement within structure 1535. After the concrete mixture sets to form structure 1535, sensing devices 1200 (disposed at different levels within the structure) continue to transmit data. The data may be received by a receiving device at the site, for example, and/or transmitted via the Internet or via a cellular network.

In other embodiments, one or more sensing devices may be added to a concrete mixture at other stages in the production, transport, and delivery process. For example, workers at a construction site may place a sensing device into a concrete mixture after the mixture has been laid at the site. Workers may drop a sensing device into the chute containing concrete as the concrete is being poured from the truck. Sensing devices may be added at other stages not discussed herein. A sensing device such as sensing device 1100 or 1200 may be added to dry components of concrete or to fluid concrete.

Figure 16:
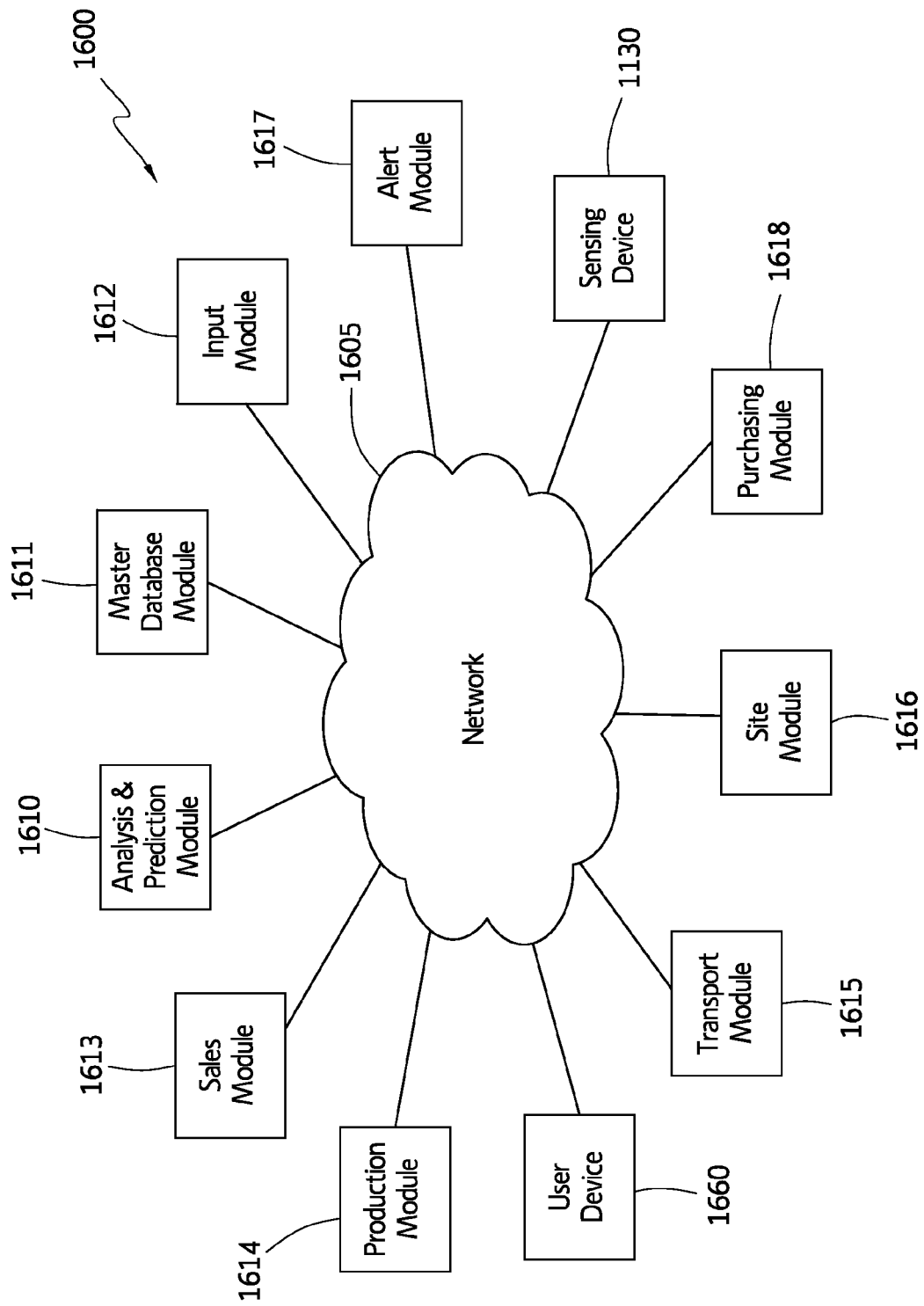
FIG. 16 shows a closed-loop production system in accordance with an embodiment.

In another embodiment, sensing devices such as sensing device 1100 or 1200 may function within a closed-loop production and delivery system. FIG. 16 shows a closed-loop production system in accordance with an embodiment. Product management system 1600 includes a master database module 1611, an input module 1612, a sales module 1613, a production module 1614, a transport module 1615, a site module 1616, an alert module 1617 and a purchasing module 1618. Production management system 1600 also includes a sensing device 1130, which may be similar to sensing device 1100 illustrated in FIG. 11 or sensing device 1200 illustrated in FIG. 12. Production management system 1600 also includes an analysis & prediction module 1610.

System 1600 may include more than one sensing device 1130. Sensing device(s) 1130 transmit data representing various measurements obtained by sensors, such measurements obtained by various sensors illustrated in FIG. 11, to master database module 1611 via a network 1605.

Production management system 1600 also includes a user device 1660, which may be a processing device such as a laptop computer, a cell phone, a personal computer, etc., employed by a user to communicate with production management system 1600.

Master database module 1611 may be implemented using a server computer equipped with a processor, a memory and/or storage, a screen and a keyboard, for example. Modules 1610-1618 may be implemented by suitable computers or other processing devices with screens for displaying and keep displaying data and keyboards for inputting data to the module.

Master database module 1611 maintains one or more product formulations associated with respective products. In the illustrative embodiment, formulations are stored in a database; however, in other embodiments, formulations may be stored in another type of data structure. Master database module 1611 also stores other data related to various aspects of production management system 1600. For example, master database module 1611 may store information concerning acceptable tolerances for various components, mixtures, production processes, etc., that may be used in system 1610 to produce various products. Stored tolerance information may include tolerances regarding technical/physical aspects of components and processes, and may also include tolerances related to costs. Master database module 1611 may also store cost data for various components and processes that may be used in system 1600.

Each module 1610-1618, as well as sensing device 1130 and user device 1660, transmit data to, and may receive data from, master database module 1611 via network 1605, which may include the Internet and/or other types of networks such as a wireless network, a wide area network, a local area network, an Ethernet network, etc.

Master database module 1611 stores data inputted from modules 1610-1618, sensing device 1130, and user device 1660. Master database module 1611 stores data in a memory or storage using a suitable data structure such as a database. In other embodiments, other data structures may be used. In some embodiments, master database module 1611 may store data remotely, for example, in a cloud-based storage network.

Analysis & prediction module 1610 analyzes data stored in master database module 1611 and generates calculations and predictions based on such information. For example, analysis & prediction module 1610 may analyze certain measurements stored in master database module 1611, such as measurements of a concrete mixture's conductivity, temperature, humidity, motion, location, elevation, etc., and generate a value of or prediction of a characteristic of a concrete mixture, such as the concrete mixture's strength, setting behavior, slump, age, maturity, etc.

Input module 1612 transmits to master database module 1611 data for storage in the form of mixture formulations associated with respective mixtures, procedures for making the mixtures, individual ingredients or components used to make the mixture, specifics about the components, the theoretical costs for each component, the costs associated with mixing the components so as to make the product or mixture, the theoretical characteristics of the product, acceptable tolerances for variations in the components used to make the product, the time for making and delivering the product to the site and costs associated shipping the product.

Sales module 1613, production module 1614, transport module 1615, and site module 1616 communicate various items of information relating to orders received from customers for specified concrete mixtures, schedules for production of the mixtures, completion of production, transport of the mixtures from production facilities to delivery sites, delivery of concrete mixtures to specified sites, use of mixtures in construction at sites, etc. Such information is stored at master database module 1611. Alert module 1617 transmits alerts to master database module 1611, to customers, and/or to others.

Production management system 1600 also includes sensing device(s) 1130. Sensing device(s) 1130 may be added to a concrete mixture at any stage of production, transport or delivery. Sensing device 1130 generates and transmits data relating to various characteristics of the concrete mixture, measurements of the environment, etc. These measurements are received by and stored at master database module 1611.

The terms "product" and "mixture" are used interchangeably herein.

Data transmitted by input module 1612 to master database module 1611 and stored in master database module 1611 may be historical in nature. Such historical data may be used by the sales personnel through sales module 1613 to make sales of a product.

In one embodiment, sales module 1613 receives product data from master database module 1611 relating to various products or mixtures that are managed by system 1600, the components that make up those products/mixtures, the theoretical costs associates with the components, making the mixture and delivery of the mixture, times for delivery of the mixture and theoretical characteristics and performance specifications of the product.

Figure 17:
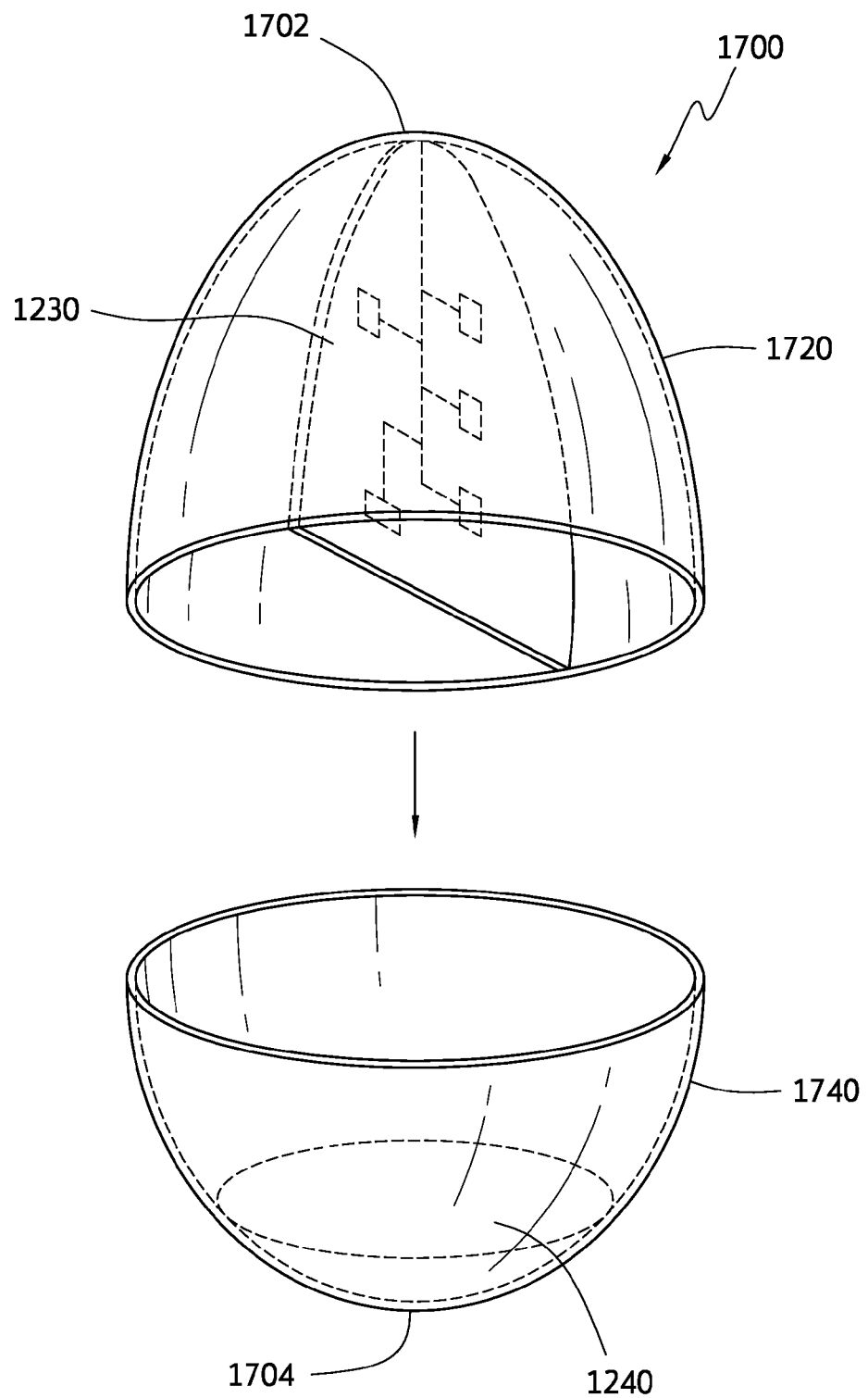
FIG. 17 shows a sensing device made of a first portion and a second portion.

In one embodiment, a sensing device similar to sensing device 1100 or 1200 may have two portions. Referring to FIG. 17, sensing device 1700 includes a first portion 1720 of the shell associated with a narrower end 1702, and a second portion 1740 of the shell associated with a flatter end 1704. The two portions of the shell may be manufactured, the plate 1230 and electronics inserted into first portion 1720, and substance 1240 inserted into second portion 1740. Electrode 1255-A is inserted in first portion 1720; electrode 1255-B is inserted in second portion 1740. The two portions 1720 and 1740 may then be joined and sealed to create a sensing device. In some embodiments, pressurized nitrogen gas may be injected into the sensing device.

In the illustrative embodiment, second portion 1740 is heavier than first portion 1720; as a result, when placed in a liquid or fluid, sensing device 1700 floats with flatter end 1704 submerged and narrower end 1702 remaining above the fluid level. In one embodiment, the second portion of the shell 1740 (having the flatter end 1704) is heavier than the first portion 1720 (having the narrower end 1702).

In other embodiments, both electrodes may be disposed in first portion 1720, or in second portion 1740.

In another embodiment, a sensing device such as sensing device 1100 or 1200 may be manufactured using three-dimensional printing technology. For example, two portions of the shell may be designed to have two portions—an upper portion associated with narrow end 1202 and a lower portion associated with flatter end 1204. Each portion may be mathematically modeled and the mathematical model then provided to a 3D printing device for production. For example, the upper portion may be mathematically defined based on an ellipsoid curve. The lower portion may be defined based on an ellipsoid curve (different from the ellipsoid curve used for the upper portion), or defined based on a circle. Other curves, or other types of mathematical formulations may be used.

In another embodiment, a production system such as that shown in FIG. 16 may maintain and offer to customers a formulation for a concrete mixture that includes several components for manufacturing concrete. The formulation may also specify a desired quantity of (i.e., one or more) sensing devices as an optional component. The formulation may also specify a stage of the manufacturing cycle (e.g., at the production plant, when the mixture is in the truck, at the construction site, etc.) at which the sensing devices are to be inserted into the mixture. If the customer orders a formulation that includes a predetermined number of sensing devices, then the concrete mixture is manufactured according to the formulation, and the predetermined number of sensing devices are added to the mixture at the specified stage in the manufacturing process (e.g., at the production facility, inserted into the mixing truck, added at the construction site, etc.)

Figure 18:
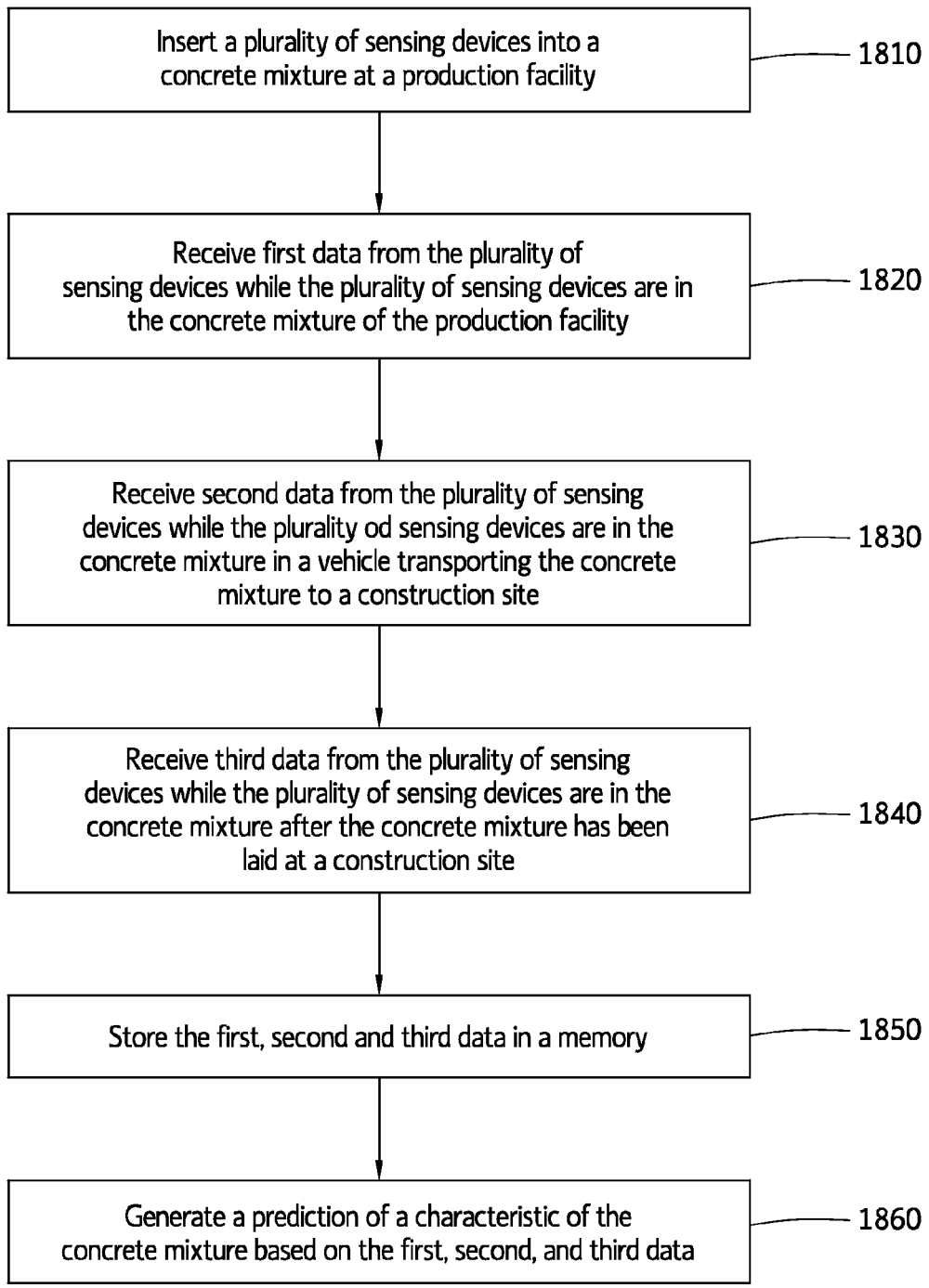
FIG. 18 is a flowchart of a method of managing a closed-loop production system in accordance with an embodiment.

FIG. 18 is a flowchart of a method of managing a closed-loop production system in accordance with an embodiment. At step 1810, a plurality of sensing devices are inserted into a concrete mixture at a production facility. Thus, as illustrated in FIG. 13, for example, a plurality of sensing devices 1200 are inserted into a concrete mixture at a production facility. In some embodiments, one or more sensing devices may be added to a dry mixture at the production facility. In other embodiments, sensing devices may be added to a wet mixture at the production facility.

At step 1820, first data is received from the plurality of sensing devices while the plurality of sensing devices are in the concrete mixture at the production facility. Sensing devices 1200 may begin to obtain measurements and transmit data immediately upon being inserted into the mixture. The data may be received by wireless receivers (not shown in FIG. 13) and transmitted to master database module 1611. At step 1830, second data is received from the plurality of sensing devices while the plurality of sensing devices are in the concrete mixture in a vehicle transporting the concrete mixture to a construction site. As illustrated in FIG. 14B, sensing devices 1200 may continue to transmit data while floating in the concrete mixture inside the drum of a mixing truck. The data is received by antenna 1435, which in turn may transmit it to master database module 1611 (or to another device in the truck which transmits it to master database module 1611.) At step 1840, third data is received from the plurality of sensing devices while the plurality of sensing devices are in the concrete mixture after the concrete mixture has been laid at a construction site. As illustrated in FIG. 15, sensing devices 1200 remain in concrete mixture 1460 while the concrete is poured at a construction site. After the concrete has been laid to form a structure 1535, sensing devices 1200 remain in the concrete and continue to transmit data. The data received from sensing devices is received by master database module 1611. At step 1850, the first, second and third data are stored in a memory. Master database module 1611 stores the data received from sensing devices at different stages of the production cycle in a memory, for example, in a database or other data structure.

At step 1860, a prediction of a characteristic of the concrete mixture is generated based on the first, second and third data. For example, analysis & prediction module 1610 may access the data generated by sensing devices 1200 and generate predictions concerning the strength, maturity, age, slump, etc., of the concrete mixture, or predictions of other characteristics. The predictions may be provided to master database module 1611 and stored, for example.

In accordance with another embodiment, data received from a plurality of sensing devices distributed throughout concrete in a building or other structure being built at a construction site as part of a project may be used to provide real-time data concerning the project. Suppose, for example, that a plurality of sensing devices are embedded in the concrete laid at different floors or levels of a building. After the concrete sets, data received from the sensing devices throughout the structure may continue to provide data concerning performance of the concrete in the structure. Such data may then be used as a basis for determining various items of information such as the strength of the concrete used in different sections of the structure, the cost of materials in different sections of the structure, the pour rate for concrete in different sections of the structure, and the pour rate cost per hour for different sections of the structure, and/or other characteristics. The data from the sensing devices may be combined with other data to generate some or all of such information. Master database module 1611 may then allow a user employing user device 1660 to access the information.

Figure 19:
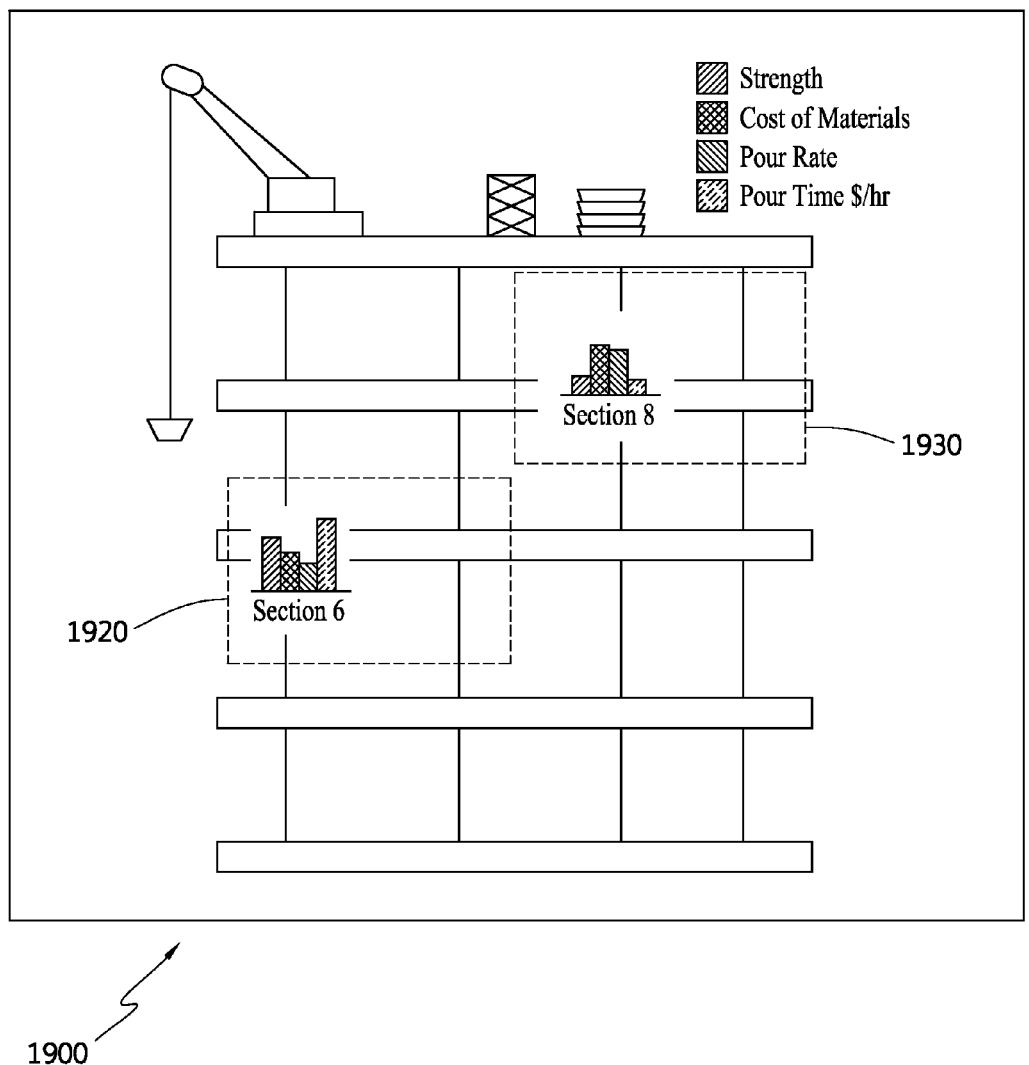
FIG. 19 shows a web page showing information related to a construction site in accordance with an embodiment.

For example, master database module 1611 may generate a web page such as that shown in FIG. 19. Web page 1900 shows a construction site that includes a building under construction. Several sections of building are defined. A user may select (by clicking on a section of the image, for example) a desired section of the structure to obtain information relating to the section. In the illustrative embodiment, the user has selected a Section 6 (1920) and a Section 8 (1930) of the structure. When the user selects a section of the structure, master database module 1611 causes a bar graph representing selected items of information relevant to the selected section to appear over the selected section in the image. In this example, a bar graph indicating strength, cost of materials, pour rate, and pour time cost per hour is displayed over the respective section. Other types of information may be displayed.

Figure 20:
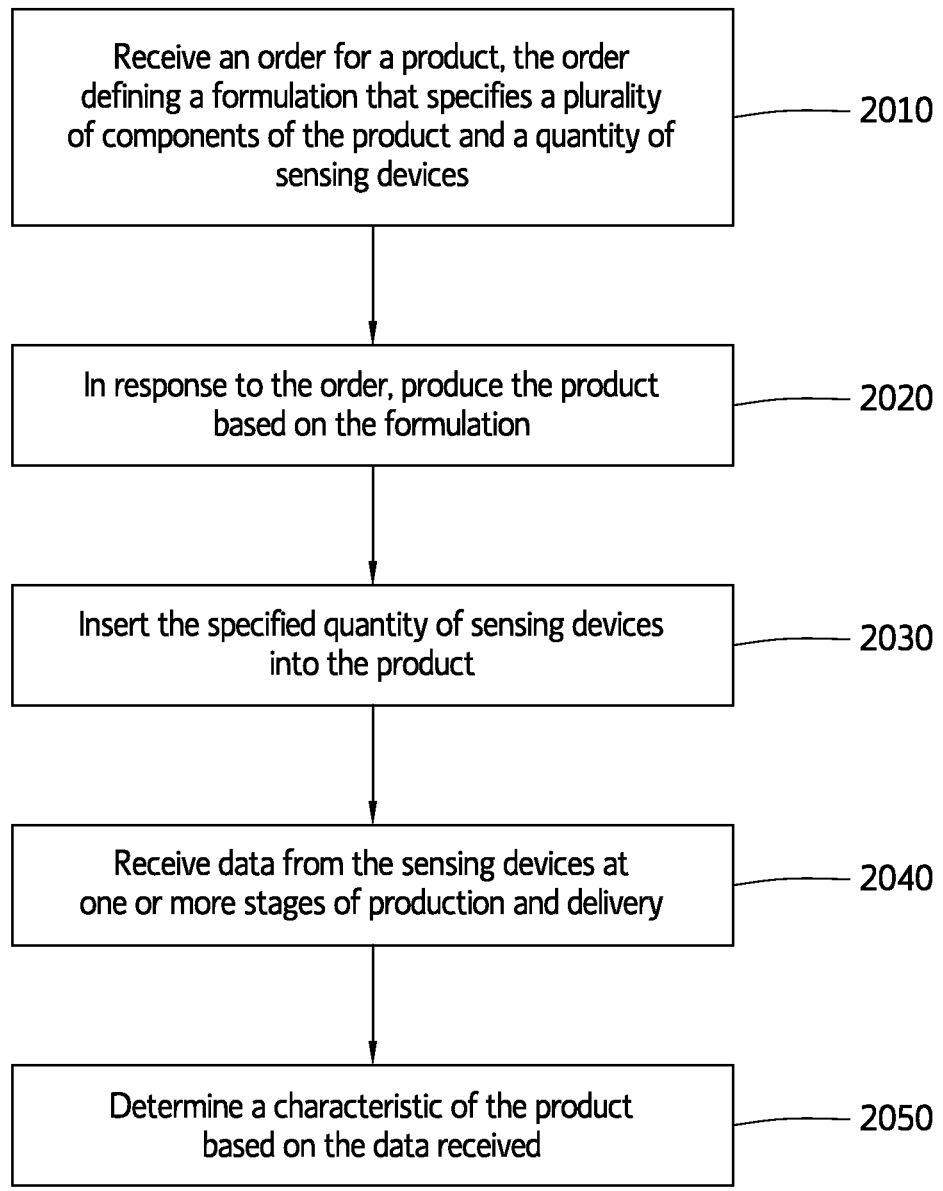
FIG. 20 shows a flowchart of a method of managing a production management system in accordance with an embodiment.

FIG. 20 is a flowchart of a method of managing a production management system in accordance with another embodiment. At step 2010, an order for a product is received, wherein the order defines a formulation that specifies a plurality of components of the product and a quantity of sensing devices. Thus, a customer may submit an order for a concrete mixture having desired components. The customer may also specify in the order a desired quantity of sensing devices to be inserted into the mixture. The order may be transmitted by sales module 1613 to master database module 1611, for example. At step 2020, in response to the order, the product is produced based on the formulation at a production facility. For example, master database module 1611 may transmit the order to a selected production facility, which receives the order and produces the product. At step 2030, the specified quantity of sensing devices are inserted into the product. Master database module 1611 may cause the specified quantity of sensing devices to be inserted into the mixture at a specified stage of production/delivery. The order may specify when and where to insert the sensing devices into the mixture. At step 2040, data is received from the sensing devices at one or more stages of production and delivery. As discussed herein, the sensing devices generate one or more measurements, which may be transmitted to master database module 1611. Master database module 1611 receives and stores the data. At step 2050, a characteristic of the product is determined based on the data. Master database module 1611 or another module may generate an estimate of strength, slump, maturity, or another characteristic, based on the data received.

In another embodiment, a sensing device similar to sensing device 1100 may function as a signal booster/retransmitter for signals received from other sensing devices. Such a sensing device may be dedicated to receiving data from other sensing devices located nearby (e.g., within a predetermined distance) and transmitting the data to the outside world (e.g., to a Bluetooth receiver, to a cellular network, etc.). In an illustrative embodiment, a predetermined percentage of sensing devices within a plurality of sensing devices (e.g., one out of five sensing devices, one out of ten sensing devices, etc.) may be adapted and/or programmed to perform a signal booster/retransmitter function. Thus, such a booster/retransmitter sensing device may receive signals from other sensing devices, optionally boost the signals, and retransmit the signals. Because wireless transmission consumes significant power, the stronger the wireless signal (longer distance) is, the more power is required. A sensing device functioning as a signal booster/retransmitter may use all or nearly all of its battery power to transmit signals over significant distances to a Bluetooth receiver or other type of receiver or network. Optionally, other sensing devices may conserve power through short haul transmission to a booster/retransmitter sensing device located within a short distance, e.g., 0.2 to 5 meters. Booster/retransmitter sensing devices may be shaped in a manner to optimize antenna efficiency.

Today a significant amounts of small polymeric and steel fibers are used to reinforce concrete and asphalt against micro cracking, and thereby increase structural longevity for public sector investments. Fibers are typically less that 1.0 mm in diameter and are up to several centimeters in length. In one embodiment, a sensing device such as sensing device 1100 may provide numerous monitoring and structural integrity related benefits to road and bridge surfaces. For example, in order to increase transmission efficiencies, fibers for addition to concrete may be specially embedded in an antenna of a sensing device. Typical steel fiber dosage to concrete is on the order 0.5 to 1 kg/m3, and the count is on the order of 2,000 (macro fiber) to more than 20,000 (micro fiber) per cubic meter. Thus, an antenna of a sensing device that includes a specially configured micro steel fiber at the rate of, e.g., 1 in 100, may result in a many device antennas dispersed through a road or bridge structure. This distribution may significantly increase the wireless transmission efficiencies of the sensing devices.

In various embodiments, the method steps described herein, including the method steps described in FIGS. 4, 5, 6, 18 and/or 20 may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 4, 5, 6, 18 and/or 20 may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 21:
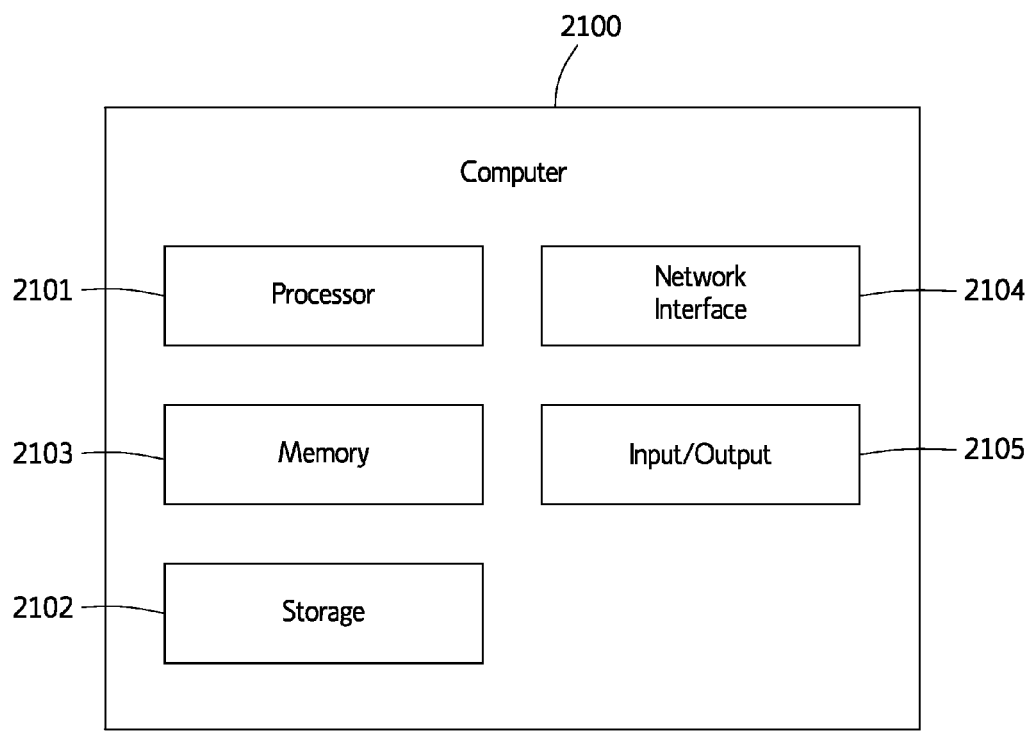
FIG. 21 shows components of an exemplary computer that may be used to implement embodiments of the invention.

A high-level block diagram of an exemplary computer that may be used to implement systems, apparatus and methods described herein is illustrated in FIG. 21. Computer 2100 includes a processor 2101 operatively coupled to a data storage device 2102 and a memory 2103. Processor 2101 controls the overall operation of computer 2100 by executing computer program instructions that define such operations. The computer program instructions may be stored in data storage device 2102, or other computer readable medium, and loaded into memory 2103 when execution of the computer program instructions is desired. Thus, the method steps of FIGS. 4, 5, 6, 18 and/or 20 can be defined by the computer program instructions stored in memory 2103 and/or data storage device 2102 and controlled by the processor 2101 executing the computer program instructions. For example, the computer program instructions can be implemented as computer executable code programmed by one skilled in the art to perform an algorithm defined by the method steps of FIGS. 4, 5, 6, 18 and/or 20. Accordingly, by executing the computer program instructions, the processor 2101 executes an algorithm defined by the method steps of FIGS. 4, 5, 6, 18 and/or 20. Computer 2100 also includes one or more network interfaces 2104 for communicating with other devices via a network. Computer 2100 also includes one or more input/output devices 2105 that enable user interaction with computer 2100 (e.g., display, keyboard, mouse, speakers, buttons, etc.).

Processor 2101 may include both general and special purpose microprocessors, and may be the sole processor or one of multiple processors of computer 2100. Processor 2101 may include one or more central processing units (CPUs), for example. Processor 2101, data storage device 2102, and/or memory 2103 may include, be supplemented by, or incorporated in, one or more application-specific integrated circuits (ASICs) and/or one or more field programmable gate arrays (FPGAs).

Data storage device 2102 and memory 2103 each include a tangible non-transitory computer readable storage medium. Data storage device 2102, and memory 2103, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 2105 may include peripherals, such as a printer, scanner, display screen, etc. For example, input/output devices 2105 may include a display device such as a cathode ray tube (CRT) or liquid crystal display (LCD) monitor for displaying information to the user, a keyboard, and a pointing device such as a mouse or a trackball by which the user can provide input to computer 2100.

Any or all of the systems and apparatus discussed herein, including master database module 1611, analysis & prediction module 1610, input module 1612, sales module 1613, production module 1614, transport module 1615, site module 1616, alert module 1617, purchase module 1618, and user device 1660, and components thereof, may be implemented using a computer such as computer 2100.

One skilled in the art will recognize that an implementation of an actual computer or computer system may have other structures and may contain other components as well, and that FIG. 21 is a high level representation of some of the components of such a computer for illustrative purposes.

While systems, apparatus, and methods are described herein in the context of a concrete mixing truck, in other embodiments, systems, apparatus and methods described herein may be used in other industries, in connection with other types of products, in other types of production facilities, in other types of vehicles and in other locations. For example, systems, apparatus, and methods described herein may be used in a vehicle (e.g., a truck) carrying other materials, including, without limitation, food products, paint, petroleum-based products, chemicals, etc. In other embodiments, systems, apparatus, and methods described herein may be used in other locations, including, without limitation, waste sites, swimming pools, sewers, culverts, pools and reservoirs used for drainage, toxic waste sites, etc.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

The invention claimed is:

1. A system comprising:
a structure comprising a concrete mixture;
a plurality of measuring devices embedded at respective locations in the concrete mixture, each measuring device comprising:
a shell comprising an elastomeric material, the shell comprising a first portion having a first end and a second portion having a second end;
wherein the first portion includes:
a thermally and electrically conducting disc;
a plate attached to the disc, the plate comprising:
a temperature sensor adapted to generate a temperature measurement;
a location sensor adapted to generate location information;
a micro-fiber composite sensor adapted to generate a measure of deformation; and
an antenna adapted to transmit data representing at least one of the temperature measurement, the location information, and the measure of deformation; and
a first electrode attached to the disc, the electrode extending through a first hole in the first portion of the shell;
wherein the second portion includes:
a predetermined quantity of a selected metallic substance embedded on the inside surface of an end of the second portion; and
a second electrode connected to the metallic substance, the second electrode extending through a second hole in the second portion of the shell; and
a processor adapted to:
receive from each respective measuring device embedded in the concrete mixture data pertaining to the concrete mixture; and
determine one or more characteristics of the concrete mixture based on the data received.

2. The system of claim 1, wherein the shell has an egg shape.

3. The system of claim 1, wherein the plate further comprises one of an impedance/conductivity sensor, a pH sensor, an accelerometer, an elevation sensor, an RFID device, a humidity sensor.

4. The system of claim 1, wherein the selected metallic substance comprises one of copper and brass.

5. The system of claim 1, wherein the thermally and electrically conducting disc is disposed perpendicular to an axis of the sensing device.

6. The system of claim 5, wherein the plate is perpendicular to the thermally and electrically conducting disc.

7. A method comprising:
inserting a plurality of sensing devices into a concrete mixture at a production facility;
receiving first data from the plurality of sensing devices while the plurality of sensing devices are in the concrete mixture at the production facility;
placing the concrete mixture and the plurality of sensing devices into a drum of a concrete mixing truck adapted to transport the concrete mixture to a construction site;
receiving, via an antenna disposed on the drum of the concrete mixing truck, second data from the plurality of sensing devices located in the concrete mixture while the concrete mixture spins in the drum, while the concrete mixing truck transports the concrete mixture to the construction site;
receiving third data from the plurality of sensing devices while the plurality of sensing devices are in the concrete mixture after the concrete mixture has been laid at the construction site;
storing the first, second and third data in a memory; and
generating a prediction of a characteristic of the concrete mixture based on the first, second and third data.

8. The method of claim 7, wherein each of the plurality of sensing devices comprises an egg-shaped shell comprising an elastomeric material, the egg-shaped shell comprising a first portion having a first end and a second portion having a second end;
wherein the first portion includes:
a thermally and electrically conducting disc;
a plate attached to the disc, the plate comprising:
a temperature sensor;
a location sensor; and
a micro-fiber composite (MFC) sensor adapted to generate a measure of deformation; and
an antenna; and
a first electrode attached to the disc, the electrode extending through a first hole in the first portion of the shell;
wherein the second portion includes:
a predetermined quantity of a selected metallic substance embedded on the inside surface of an end of the second portion; and
a second electrode connected to the metallic substance, the second electrode extending through a second hole in the second portion of the shell.

9. The method of claim 7, further comprising:
causing the concrete mixture and the plurality of sensing devices to be transported on a vehicle.

10. The method of claim 7, wherein the characteristic includes one of concrete maturity, concrete strength, and slump.

11. The method of claim 7, further comprising:
receiving from the MFC sensor fourth data representing a deformation;
determining an estimate of a slump of the concrete mixture based on the fourth data; and
determining an estimate of a mixing energy of mixing concrete.

12. A method of managing a closed-loop production and delivery system, the method comprising:
receiving an order for a concrete mixture, the order defining a formulation that specifies a plurality of components of the product and a quantity of sensing devices;
in response to the order, producing the concrete mixture at a production facility based on the formulation;
inserting the specified quantity of sensing devices into the concrete mixture at the production facility;
receiving first data from the sensing devices while the sensing devices are in the concrete mixture at the production facility, second data from the sensing devices while the sensing devices are in the concrete mixture during transportation of the concrete mixture in a concrete mixing truck, and third data from the sensing devices while the sensing devices are in the concrete mixture after the concrete mixture has been laid at a construction site; and determining a characteristic of the concrete mixture based on the first, second, and third data.

13. The method of claim 12, wherein each sensing devices includes an egg shaped sensing device that includes a temperature sensor and an antenna.

14. The method of claim 12, wherein the characteristic includes one of concrete maturity, concrete strength and slump.

15. A communication system comprising:
   a concrete mixing truck comprising a drum adapted to hold a concrete mixture;
   at least one sensing device disposed inside the drum of the concrete mixing truck, the at least one sensing device being adapted to float within a concrete mixture inside the drum, to generate data relating to the concrete mixture, and to transmit a signal comprising the data;
   an antenna device disposed on the drum, the antenna device comprising:
      a receiver component adapted to receive the signal from the at least one device located in the concrete mixture inside the drum; and
      a transmitter component adapted to retransmit the signal outside the drum; and
   a communication device adapted to receive the signal retransmitted by the transmitter component of the antenna device and transmit the signal via a network to a second device.

16. The communication system of claim 15, wherein the antenna device comprises a Bluetooth antenna device.

* * * * *